(12) United States Patent
Karelson et al.

(10) Patent No.: US 7,786,292 B2
(45) Date of Patent: Aug. 31, 2010

(54) ANTISENSE AGENTS COMBINING STRONGLY BOUND BASE-MODIFIED OLIGONUCLEOTIDE AND ARTIFICIAL NUCLEASE

(75) Inventors: Mati Karelson, Tartumaa (EE); Mart Saarma, Helsinki (FI); Mehis Pilv, Tallinn (EE)

(73) Assignee: Baltic Technology Development, Ltd., Tallinn (EE)

( * ) Notice: Subject to any disclaimer, the term of this patent is extended or adjusted under 35 U.S.C. 154(b) by 0 days.

(21) Appl. No.: 11/742,384

(22) Filed: Apr. 30, 2007

(65) Prior Publication Data
US 2007/0259830 A1    Nov. 8, 2007

Related U.S. Application Data

(60) Provisional application No. 60/797,448, filed on May 3, 2006.

(51) Int. Cl.
*C07H 21/04* (2006.01)
*C07H 21/00* (2006.01)
*A61K 31/70* (2006.01)

(52) U.S. Cl. .................. 536/24.5; 536/23.1; 536/25.3; 514/44

(58) Field of Classification Search .................. None
See application file for complete search history.

(56) References Cited

U.S. PATENT DOCUMENTS

| | | | |
|---|---|---|---|
| 3,687,808 A | 8/1972 | Merigan et al. |
| 4,426,330 A | 1/1984 | Sears |
| 4,469,863 A | 9/1984 | Ts'o et al. |
| 4,476,301 A | 10/1984 | Imbach et al. |
| 4,534,899 A | 8/1985 | Sears |
| 4,587,044 A | 5/1986 | Miller et al. |
| 4,605,735 A | 8/1986 | Miyoshi et al. |
| 4,667,025 A | 5/1987 | Miyoshi et al. |
| 4,762,779 A | 8/1988 | Snitman |
| 4,789,737 A | 12/1988 | Miyoshi et al. |
| 4,824,941 A | 4/1989 | Gordon et al. |
| 4,828,979 A | 5/1989 | Klevan et al. |
| 4,835,263 A | 5/1989 | Nguyen et al. |
| 4,845,205 A | 7/1989 | Huynh Dinh et al. |
| 4,876,335 A | 10/1989 | Yamane et al. |
| 4,904,582 A | 2/1990 | Tullis |
| 4,948,882 A | 8/1990 | Ruth |
| 4,958,013 A | 9/1990 | Letsinger |
| 4,981,957 A | 1/1991 | Lebleu et al. |
| 5,013,556 A | 5/1991 | Woodle et al. |
| 5,023,243 A | 6/1991 | Tullis |
| 5,034,506 A | 7/1991 | Summerton et al. |
| 5,082,830 A | 1/1992 | Brakel et al. |
| 5,108,921 A | 4/1992 | Low et al. |
| 5,109,124 A | 4/1992 | Ramachandran et al. |
| 5,112,963 A | 5/1992 | Pieles et al. |
| 5,118,800 A | 6/1992 | Smith et al. |
| 5,118,802 A | 6/1992 | Smith et al. |
| 5,130,302 A | 7/1992 | Spielvogel et al. |
| 5,134,066 A | 7/1992 | Rogers et al. |
| 5,138,045 A | 8/1992 | Cook et al. |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,185,444 A | 2/1993 | Summerton et al. |
| 5,188,897 A | 2/1993 | Suhadolnik et al. |
| 5,194,599 A | 3/1993 | Froehler et al. |
| 5,213,804 A | 5/1993 | Martin et al. |
| 5,214,134 A | 5/1993 | Weis et al. |
| 5,214,136 A | 5/1993 | Lin et al. |
| 5,216,141 A | 6/1993 | Benner |
| 5,218,105 A | 6/1993 | Cook et al. |
| 5,227,170 A | 7/1993 | Sullivan |
| 5,235,033 A | 8/1993 | Summerton et al. |
| 5,245,022 A | 9/1993 | Weis et al. |
| 5,254,469 A | 10/1993 | Warren, III et al. |
| 5,258,506 A | 11/1993 | Urdea et al. |
| 5,262,536 A | 11/1993 | Hobbs, Jr. |
| 5,264,221 A | 11/1993 | Tagawa et al. |
| 5,264,423 A | 11/1993 | Cohen et al. |
| 5,264,562 A | 11/1993 | Matteucci |

(Continued)

FOREIGN PATENT DOCUMENTS

EP    0 680 969    11/1995

(Continued)

OTHER PUBLICATIONS

Delehanty et al., "RNA hydrolysis and inhibition of translation by a Co (III)-cyclen complex." *RNA*. 11: 831-6 (2005).
Hicke et al., "Tumor targeting by an aptamer." *J. Nucl. Med.* 47: 668-78 (2006).
Hjelstuen et al., "Comparative evaluation of 99mTc-MAG2-oligonucleotides with phophodiester or phosphorothioate backbones: preparation, stability and biodistribution." *Journal of Labeled Compounds and Radiopharmaceuticals*. 42: 737-60 (1999).
Mardirossian et al., In vivo hybridization of Technetium-99m-labeled peptide nucleic acid (PNA) *J. Nucl. Med.* 38: 907-13 (1997).
Roivainen et al., "68Ga-labeled oligonucleotides for in vivo imaging with PET." *J. Nucl. Med.* 45: 347-55 (2004).

(Continued)

*Primary Examiner*—Tracy Vivlemore
(74) *Attorney, Agent, or Firm*—Marshall, Gerstein & Borun LLP

(57) ABSTRACT

The present invention provides compounds having a chelating moiety and an oligonucleotide sequence wherein the oligonucleotide includes one or more modified nucleobases, such as hydroxynucleobases. The disclosed compounds are suitable for antisense therapy. The chelating moiety can be complexed to an ion of a lanthanide metal. These compounds are efficient translation inhibitors of nucleic acids and have increased binding affinity for target nucleic acids. The invention also includes compositions and methods of using these compositions as antisense therapy.

37 Claims, 2 Drawing Sheets

U.S. PATENT DOCUMENTS

| | | |
|---|---|---|
| 5,264,564 A | 11/1993 | Matteucci |
| 5,272,250 A | 12/1993 | Spielvogel et al. |
| 5,276,019 A | 1/1994 | Cohen et al. |
| 5,278,302 A | 1/1994 | Caruthers et al. |
| 5,286,717 A | 2/1994 | Cohen et al. |
| 5,292,873 A | 3/1994 | Rokita et al. |
| 5,317,098 A | 5/1994 | Shizuya et al. |
| 5,319,080 A | 6/1994 | Leumann |
| 5,321,131 A | 6/1994 | Agrawal et al. |
| 5,354,844 A | 10/1994 | Beug et al. |
| 5,356,633 A | 10/1994 | Woodle et al. |
| 5,359,044 A | 10/1994 | Cook et al. |
| 5,367,066 A | 11/1994 | Urdea et al. |
| 5,371,241 A | 12/1994 | Brush |
| 5,391,723 A | 2/1995 | Priest |
| 5,393,878 A | 2/1995 | Leumann |
| 5,395,619 A | 3/1995 | Zalipsky et al. |
| 5,399,676 A | 3/1995 | Froehler |
| 5,405,938 A | 4/1995 | Summerton et al. |
| 5,414,077 A | 5/1995 | Lin et al. |
| 5,416,016 A | 5/1995 | Low et al. |
| 5,416,203 A | 5/1995 | Letsinger |
| 5,417,978 A | 5/1995 | Tari et al. |
| 5,432,272 A | 7/1995 | Benner |
| 5,434,257 A | 7/1995 | Matteucci et al. |
| 5,446,137 A | 8/1995 | Maag et al. |
| 5,451,463 A | 9/1995 | Nelson et al. |
| 5,453,496 A | 9/1995 | Caruthers et al. |
| 5,455,233 A | 10/1995 | Spielvogel et al. |
| 5,457,187 A | 10/1995 | Gmeiner et al. |
| 5,459,127 A | 10/1995 | Felgner et al. |
| 5,459,255 A | 10/1995 | Cook et al. |
| 5,462,854 A | 10/1995 | Coassin et al. |
| 5,466,677 A | 11/1995 | Baxter et al. |
| 5,466,786 A | 11/1995 | Buhr et al. |
| 5,469,854 A | 11/1995 | Unger et al. |
| 5,470,967 A | 11/1995 | Huie et al. |
| 5,476,925 A | 12/1995 | Letsinger et al. |
| 5,484,908 A | 1/1996 | Froehler et al. |
| 5,486,603 A | 1/1996 | Buhr |
| 5,489,677 A | 2/1996 | Sanghvi et al. |
| 5,502,177 A | 3/1996 | Matteucci et al. |
| 5,510,475 A | 4/1996 | Agrawal et al. |
| 5,512,295 A | 4/1996 | Kornberg et al. |
| 5,512,439 A | 4/1996 | Hornes et al. |
| 5,512,667 A | 4/1996 | Reed et al. |
| 5,514,785 A | 5/1996 | Van Ness et al. |
| 5,519,126 A | 5/1996 | Hecht |
| 5,519,134 A | 5/1996 | Acevedo et al. |
| 5,521,291 A | 5/1996 | Curiel et al. |
| 5,525,465 A | 6/1996 | Haralambidis et al. |
| 5,525,711 A | 6/1996 | Hawkins et al. |
| 5,527,528 A | 6/1996 | Allen et al. |
| 5,527,899 A | 6/1996 | Froehler |
| 5,534,259 A | 7/1996 | Zalipsky et al. |
| 5,536,821 A | 7/1996 | Agrawal et al. |
| 5,539,082 A | 7/1996 | Nielsen et al. |
| 5,541,306 A | 7/1996 | Agrawal et al. |
| 5,541,307 A | 7/1996 | Cook et al. |
| 5,541,313 A | 7/1996 | Ruth |
| 5,543,152 A | 8/1996 | Webb et al. |
| 5,543,158 A | 8/1996 | Gref et al. |
| 5,545,730 A | 8/1996 | Urdea et al. |
| 5,547,932 A | 8/1996 | Curiel et al. |
| 5,550,111 A | 8/1996 | Suhadolnik et al. |
| 5,552,538 A | 9/1996 | Urdea et al. |
| 5,552,540 A | 9/1996 | Haralambidis |
| 5,556,948 A | 9/1996 | Tagawa et al. |
| 5,561,225 A | 10/1996 | Maddry et al. |
| 5,563,253 A | 10/1996 | Agrawal et al. |
| 5,565,552 A | 10/1996 | Magda et al. |
| 5,565,555 A | 10/1996 | Froehler et al. |
| 5,567,810 A | 10/1996 | Weis et al. |
| 5,567,811 A | 10/1996 | Misiura et al. |
| 5,571,799 A | 11/1996 | Tkachuk et al. |
| 5,574,142 A | 11/1996 | Meyer, Jr. et al. |
| 5,576,427 A | 11/1996 | Cook et al. |
| 5,578,717 A | 11/1996 | Urdea et al. |
| 5,578,718 A | 11/1996 | Cook et al. |
| 5,580,575 A | 12/1996 | Unger et al. |
| 5,580,731 A | 12/1996 | Chang et al. |
| 5,583,020 A | 12/1996 | Sullivan |
| 5,585,481 A | 12/1996 | Arnold, Jr. et al. |
| 5,587,361 A | 12/1996 | Cook et al. |
| 5,587,371 A | 12/1996 | Sessler et al. |
| 5,587,469 A | 12/1996 | Cook et al. |
| 5,591,584 A | 1/1997 | Chang et al. |
| 5,591,721 A | 1/1997 | Agrawal et al. |
| 5,591,722 A | 1/1997 | Montgomery et al. |
| 5,594,121 A | 1/1997 | Froehler et al. |
| 5,595,726 A | 1/1997 | Magda et al. |
| 5,595,756 A | 1/1997 | Bally et al. |
| 5,596,086 A | 1/1997 | Matteucci et al. |
| 5,596,091 A | 1/1997 | Switzer |
| 5,597,696 A | 1/1997 | Linn et al. |
| 5,597,909 A | 1/1997 | Urdea et al. |
| 5,599,923 A | 2/1997 | Sessler et al. |
| 5,599,928 A | 2/1997 | Hemmi et al. |
| 5,602,240 A | 2/1997 | De Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,623,070 A | 4/1997 | Cook et al. |
| 5,625,050 A | 4/1997 | Beaton et al. |
| 5,627,053 A | 5/1997 | Usman et al. |
| 5,633,360 A | 5/1997 | Bischofberger et al. |
| 5,639,873 A | 6/1997 | Barascut et al. |
| 5,645,985 A | 7/1997 | Froehler et al. |
| 5,646,265 A | 7/1997 | McGee |
| 5,646,269 A | 7/1997 | Matteucci et al. |
| 5,658,873 A | 8/1997 | Bertsch-Frank et al. |
| 5,663,312 A | 9/1997 | Chaturvedula |
| 5,670,633 A | 9/1997 | Cook et al. |
| 5,672,697 A | 9/1997 | Buhr et al. |
| 5,677,437 A | 10/1997 | Teng et al. |
| 5,677,439 A | 10/1997 | Weis et al. |
| 5,681,940 A | 10/1997 | Wang et al. |
| 5,681,941 A | 10/1997 | Cook et al. |
| 5,684,149 A | 11/1997 | Morrow |
| 5,688,941 A | 11/1997 | Cook et al. |
| 5,700,920 A | 12/1997 | Altmann et al. |
| 5,714,331 A | 2/1998 | Buchardt et al. |
| 5,719,262 A | 2/1998 | Buchardt et al. |
| 5,721,218 A | 2/1998 | Froehler |
| 5,750,692 A | 5/1998 | Cook et al. |
| 5,763,588 A | 6/1998 | Matteucci et al. |
| 5,770,713 A | 6/1998 | Imbach et al. |
| 5,792,608 A | 8/1998 | Swaminathan et al. |
| 5,792,747 A | 8/1998 | Schally et al. |
| 5,830,653 A | 11/1998 | Froehler et al. |
| 5,856,099 A * | 1/1999 | Miraglia et al. ................ 435/6 |
| 5,925,744 A | 7/1999 | Haner et al. |
| 6,005,096 A | 12/1999 | Matteucci et al. |
| 6,031,086 A | 2/2000 | Switzer |
| 6,083,923 A * | 7/2000 | Hardee et al. ................ 514/44 |
| 6,117,992 A | 9/2000 | Iyer |
| 6,127,121 A | 10/2000 | Meyer et al. |
| 6,232,463 B1 | 5/2001 | Cook et al. |
| 6,235,887 B1 | 5/2001 | Froehler et al. |
| 6,287,860 B1 | 9/2001 | Monia et al. |
| 6,395,492 B1 | 5/2002 | Manoharan et al. |
| 6,579,704 B2 | 6/2003 | Short |

| | | |
|---|---|---|
| 6,656,730 B1 | 12/2003 | Manoharan |
| 6,747,014 B2 | 6/2004 | Teng et al. |
| 6,841,539 B1 * | 1/2005 | Mehta et al. ............... 514/44 |
| 6,887,906 B1 | 5/2005 | Teng et al. |
| 6,984,734 B2 | 1/2006 | Sessler et al. |
| 2003/0027780 A1 | 2/2003 | Hardee et al. |
| 2004/0121357 A1 | 6/2004 | Franklin |
| 2004/0171030 A1 | 9/2004 | Baker et al. |
| 2004/0248094 A1 * | 12/2004 | Ford et al. ............... 435/6 |
| 2006/0094045 A1 | 5/2006 | Chang et al. |

FOREIGN PATENT DOCUMENTS

| | | |
|---|---|---|
| WO | WO-93/07883 | 4/1993 |
| WO | WO-93/24510 | 12/1993 |
| WO | WO-94/26764 | 11/1994 |
| WO | WO-98/39352 | 9/1998 |
| WO | WO-99/14226 | 3/1999 |
| WO | WO 03/100017 | 12/2003 |
| WO | WO 03/106477 | 12/2003 |
| WO | WO 2006/091915 | 8/2006 |

OTHER PUBLICATIONS

Suzuki et al., "imaging endogenous gene expression in brain cancer in vivo with 111 In-peptide nucleic acid antisense radiopharmaceuticals and brain drug-targeting technology." *J. Nucl. Med.* 45: 1766-75 (2004).

Tian et al., "Imaging oncogene expression." *Ann. N Y Acad. Sci.* 1002:165-88 (2003).

Urban et al., "Structural modifications of antisense oligonucleotides." *IL Farmco* 58: 243-58 (2003).

Zhang et al., "Construction of a novel chimera consisting of a chelator-containing Tat peptide conjugated to a morpholine antisense oligomer for Technetium-99m labeling and accelerating cellular kinetics." *Nucl. Med. Biol.* 33: 263-9 (2006).

Zhang et al., "Uptake kinetics of 99mTc-MAG3-antisense oligonucleotide to PCNA and effect on gene expression in vascular smooth cells." *J. Nucl. Med.* 46:1052-8 (2005).

PCT Search Report and Written Opinion, PCT/FI2007/050231, Apr. 12, 2007.

Altschul et al., "Basic Local Alignment Search Tool", *J. Mol. Biol.*, 215:403-410 (1990).

Baker et al., "Oligonucleotide-europium complex conjugate designed to cleave the 5' cap structure of the ICAM-1 transcript potentiates antisense activity in cells," *Nucleic Acids Research*, 27:1547-1551 (1999).

Brazma et al., "Gene expression data analysis," *FEBS Lett.*, 480:17-24 (2000).

Canaple et al., "Artificial Ribonucleases: efficient and specific in vitro cleavage of human c-raf-1 RNA", *Bioconjug. Chem.*, 13:945-951 (2002).

Carulli et al., "High Throughput Analysis of Differential Gene Expression", *J. Cell Biochem. Suppl.*, 30-31:286-296 (1998).

Celis et al., "Gene expression profiling: monitoring transcription and translation products using DNA microarrays and proteomics," *FEBS Lett.*, 480:2-16 (2000).

Cowan, "Chemical nucleases", *Curr. Opin. Chem. Biol.*, 5:634-642 (2001).

Crooke, "Progress in antisense therapeutics", *Med. Res. Rev.*, 16:319-344 (1996).

Englisch et al., "Chemically Modified Oligonucleotides as Probes and Inhibitors", *Angewandte Chemie*, International Edition, 30:613 (1991).

Fire et al., "Potent and specific genetic interference by double-stranded RNA in *Caenorhabditis elegans*," *Nature*, 391:806-811 (1998).

Franklin, "Lanthanide-mediated DNA hydrolysis", *Curr. Opin. Chem. Biol.*, 5:201-208 (2001).

Fuchs et al., "Identification of differentially expressed genes by mutually subtracted RNA fingerprinting", *Anal. Biochem.*, 286:91-98 (2000).

GenBank accession No. AB264547, *Nicotiana tabacum* NtMEK2 mRNA for mitogen-activated protein kinase 2, complete cds; Mar. 24, 2007.

GenBank accession No. BC107069, *Homo sapiens* v-abl Abelson murine leukemia viral oncogene homolog 1, mRNA (cDNA clone Image:40009788), partial cds; Apr. 11, 2007.

GenBank accession No. CH471062, *Homo sapiens* 211000035832302 genomic scaffold, whole genome shotgun sequence; Dec. 18, 2006.

GenBank accession No. DQ531584, *Karenia brevis* flavodoxin protein precursor (FLV) mRNA, complete cds; Oct. 8, 2006.

GenBank accession No. DQ902653, Foot-and-mouth disease virus—type O isolate UZ05P13a-5dpi VP2 gene, partial cds; Apr. 5, 2007.

GenBank accession No. EF432550, *Homo sapiens* FEM-07-NIGEB3 tumor protein p53 (TP53) gene, intron 3; Mar. 12, 2007.

GenBank accession No. EF470241, *Potato virus Y* isolate SD4 Nlb protein gene, partial cds; Apr. 3, 2007.

GenBank accession No. NC_002034, *Cucumber mosaic virus* RNA 1, complete sequence; Mar. 30, 2007.

GenBank accession No. NG_005905, *Homo sapiens* breast cancer 1, early onset (BRCA1); and partial neighbor of BRCA1 gene 2 (NBR2); and ribosomal protein L21 pseudogene 4 (RPL21P4), on chromosome 17; Jun. 22, 2007.

GenBank accession No. NM_000038, *Homo sapiens* adenomatosis polyposis coli (APC), mRNA; Aug. 12, 2007.

GenBank accession No. NM_000321, *Homo sapiens* retinoblastoma 1 (including osteosarcoma) (RB1), mRNA; Aug. 12, 2007.

GenBank accession No. NM_001001890, *Homo sapiens* runt-related transcription factor 1 (acute myeloid leukemia 1; aml1 oncogene) (RUNX1), transcript variant 2, mRNA; Aug. 12, 2007.

GenBank accession No. NM_001033082, *Homo sapiens* v-myc myelocytomatosis viral oncogene homolog 1, lung carcinoma derived (avian) (MYCL1), transcript variant 2, mRNA; Jul. 30, 2007.

GenBank accession No. NM_001042771, *Homo sapiens* lymphocyte-specific protein tyrosine kinase (LCK), transcript variant 1, mRNA; Aug. 12, 2007.

GenBank accession No. NM_001080547, *Homo sapiens* spleen focus forming virus (SFFV) proviral integration oncogene spi1 (SPI1), transcript variant 1, mRNA; Aug. 6, 2007.

GenBank accession No. NM_002336, *Homo sapiens* low density lipoprotein receptor-related protein 6 (LRP6), mRNA; Aug. 6, 2007.

GenBank accession No. NM_002524, *Homo sapiens* neuroblastoma RAS viral (v-ras) oncogene homolog (NRAS), mRNA; Aug. 6, 2007.

GenBank accession No. NM_002648, *Homo sapiens* pim-1 oncogene (PIM1), mRNA; Jul. 30, 2007.

GenBank accession No. NM_003189, *Homo sapiens* T-cell acute lymphocytic leukemia 1 (TAL1), mRNA; Jul. 1, 2007.

GenBank accession No. NM_003965, *Homo sapiens* chemokine (C-C motif) receptor-like 2 (CCRL2), mRNA; Jun. 26, 2007.

GenBank accession No. NM_004119, *Homo sapiens* fms-related tyrosine kinase 3 (FLT3), mRNA; Jul. 31, 2007.

GenBank accession No. NM_004232, *Homo sapiens* suppressor of cytokine signaling 6 (SOCS6), mRNA; Jun. 27, 2007.

GenBank accession No. NM_005238, *Homo sapiens* v-ets erythroblastosis virus E26 oncogene homolog 1 (avian) (ETS1), mRNA; Jul. 30, 2007.

GenBank accession No. NM_005359, *Homo sapiens* SMAD family member 4 (SMAD4), mRNA; Aug. 12, 2007.

GenBank accession No. NM_005378, *Homo sapiens* v-myc myelocytomatosis viral related oncogene, neuroblastoma derived (avian) (MYCN), mRNA; Jul. 30, 2007.

GenBank accession No. NM_005521, *Homo sapiens* T-cell leukemia homeobox 1 (TLX1), mRNA; Jul. 30, 2007.

GenBank accession No. NM_006106, *Homo sapiens* Yes-associated protein 1, 65kDa (YAP1), mRNA; Aug. 6, 2007.

GenBank accession No. NM_007069, *Homo sapiens* HRAS-like suppressor 3 (HRASLS3), mRNA; Jun. 26, 2007.

GenBank accession No. NM_007305, *Homo sapiens* breast cancer 1, early onset (BRCA1), transcript variant BRCA1-delta9-10-11b, mRNA; Aug. 12, 2007.

GenBank accession No. NM_012081, *Homo sapiens* elongation factor, RNA polymerase II, 2 (ELL2), mRNA; Aug. 14, 2007.

GenBank accession No. NM_014520, *Homo sapiens* MYB binding protein (P160) 1a (MYBBP1A), mRNA; Jun. 26, 2007.
GenBank accession No. NM_016363, *Homo sapiens* glycoprotein VI (platelet) (GP6), transcript variant 2, mRNA; Jun. 27, 2007.
GenBank accession No. NM_016848, *Homo sapiens* SHC (Src homology 2 domain containing) transforming protein 3 (SHC3), mRNA; Jul. 1, 2007.
GenBank accession No. NM_017940, *Homo sapiens* neuroblastoma breakpoint family, member 1 (NBPF1), mRNA; Jun. 27, 2007.
GenBank accession No. NM_017956, *Homo sapiens* tRNA methyltransferase 12 homolog (*S. cerevisiae*) (TRMT12), mRNA; Aug. 6, 2007.
GenBank accession No. NM_020630, *Homo sapiens* ret proto-oncogene (RET), transcript variant 4, mRNA; Aug. 12, 2007.
GenBank accession No. NM_021724, *Homo sapiens* nuclear receptor subfamily 1, group D, member 1 (NR1D1), mRNA; Jun. 27, 2007.
GenBank accession No. NM_021966, *Homo sapiens* T-cell leukemia/lymphoma 1A (TCL1A), transcript variant 1, mRNA; Jun. 26, 2007.
GenBank accession No. NM_022045, *Homo sapiens* Mdm2, transformed 3T3 cell double minute 2, p53 binding protein (mouse) binding protein, 104kDa (MTBP), mRNA; Jun. 26, 2007.
GenBank accession No. NM_022132, *Homo sapiens* methylcrotonoyl-Coenzyme A carboxylase 2 (beta) (MCCC2), mRNA; Jun. 26, 2007.
GenBank accession No. NM_024426, *Homo sapiens* Wilms tumor 1 (WT1), transcript variant D, mRNA; Aug. 12, 2007.
GenBank accession No. NM_032789, *Homo sapiens* poly (ADP-ribose) polymerase family, member 10 (PARP10), mRNA; Jun. 26, 2007.
GenBank accession No. NM_053056, *Homo sapiens* cyclin D1 (CCND1), mRNA; Aug. 12, 2007.
GenBank accession No. NM_138392, *Homo sapiens* SH3KBP1 binding protein 1 (SHKBP1), mRNA; Jun. 26, 2007.
GenBank accession No. NM_138573, *Homo sapiens* neuregulin 4 (NRG4), mRNA; Jun. 27, 2007.
GenBank accession No. NM_138931, *Homo sapiens* B-cell CLL/lymphoma 6 (zinc finger protein 51) (BCL6), transcript variant 2 mRNA; Jul. 30, 2007.
GenBank accession No. NM_153048, *Homo sapiens* FYN oncogene related to SRC, FGR, YES (FYN), transcript variant 3, mRNA; Aug. 12, 2007.
GenBank accession No. NM_176795, *Homo sapiens* v-Ha-ras Harvey rat sarcoma viral oncogene homolog (HRAS), transcript variant 3, mRNA; Aug. 12, 2007.
GenBank accession No. NM_181505, *Homo sapiens* protein phosphatase 1, regulatory (inhibitor) subunit 1B (dopamine and cAMP regulated phosphoprotein, DARPP-32) (PPP1R1B), transcript variant 2, mRNA; Jul. 30, 2007.
GenBank accession No. NM_181831, *Homo sapiens* neurofibromin 2 (bilateral acoustic neuroma) (NF2), transcript variant 13, mRNA; Aug. 6, 2007.
Going et al., "Molecular pathology and future developments", *Eur. J. Cancer*, 35:1895-1904 (1999).
Guo et al., "par-1, a gene required for establishing polarity in *C. elegans* embryos, encodes a putative Ser/Thr kinase that is asymmetrically distributed," *Cell*, 81:611-620 (1995).
Hall et al., "Towards artificial ribonucleases: the sequence-specific cleavage of RNA in a duplex," *Nucleic Acids Research*, 24:3522-3526 (1996).
Hall et al., "Efficient sequence-specific cleavage of RNA using novel europium complexes conjugated to oligonucleotides", *Chem. Biol.*, 1:185-190 (1994).
Hall et al., "Sequence-specific cleavage of RNA using macrocyclic lanthanide complexes conjugated to oligonucleotides: a structure activity study", *Nucleosides & Nucleotides*, 16:1357-1368 (1997).
Häner et al., "The sequence-specific cleavage of RNA by artificial chemical ribonucleases", *Antisense Nucleic Acid Drug Dev.*, 7:423-430 (1997).
Haner et al., "Development of artificial ribonucleases using macrocyclic lanthanide complexes", *Chimia*, 54:569-573 (2000).

Hegg et al., "Toward the development of metal-based synthetic nucleases and peptidases: a rationale and progress report in applying the principles of coordination chemistry", *Coord. Chem. Revs.*, 173:133-165 (1998).
Jungblut et al., "Proteomics in human disease: cancer, heart and infectious diseases", *Electrophoresis*, 20:2100-2110 (1999).
Jurecic et al., "Long-distance DD-PCR and cDNA microarrays", *Curr. Opin. Microbiol.*, 3:316-321 (2000).
Karelson et al., "Quantum-chemical modeling of the tautomeric equilibria of modified anionic nucleic acid bases," *ARKIVOC*, 2001: 51-62 (2001).
Komiyama et al., "Progress towards synthetic enzymes for phosphoester hydrolysis", *Curr. Opin. Chem. Biol.*, 2:751-757 (1998).
Komiyama, Sequence-specific and hydrolytic scission of DNA and RNA by lanthanide complex-oligoDNA hybrids, *J. Biochem. (Tokyo)*, 118:665-670 (1995).
Kuzuya et al., "Conjugation of various acridines to DNA for site-selective RNA scission by lanthanide ion", *Bioconjug. Chem.*, 13:365-369 (2002).
Kuzuya et al., "Selective activation of two sites in RNA by acridine-bearing oligonucleotides for clipping of designated RNA fragments", *J. Am. Chem. Soc.*, 126:1430-1436 (2004).
Larson et al., "Rapid DNA fingerprinting of pathogens by flow cytometry", *Cytometry*, 41:203-208 (2000).
Larsson et al., "High-throughput protein expression of cDNA products as a tool in functional genomics", *J. Biotechnol.*, 80:143-157 (2000).
Madden et al., "Serial analysis of gene expression: from gene discovery to target identification", *Drug Discov. Today*, 5:415-425 (2000).
Magda et al., "Metal complex conjugates of antisense DNA which display ribosyme-like activity", *J. Am. Chem. Soc.*, 119:6947-6948 (1997).
Martin, "38. Ein Neuer Zugang zu 2'-O-Alkylribonucleosiden und Eigenschaften deren Oligonucleotide", *Helv. Chim. Acta*, 78:486-504 (1995).
Mesmaekar et al., "Antisense oligonucleotides", *Acc. Chem. Res.*, 28:366-374 (1995).
Montgomery et al., "RNA as a target of double-stranded RNA-mediated genetic interference in *Caenorhabditis elegans*," *Proc. Natl. Acad. Sci. USA*, 95:15502-15507 (1998).
Morrow, "Artificial ribonucleases", *Adv. Inorg. Biochem.*, 9:41-74 (1994).
Nielsen et al., "Sequence-selective recognition of DNA by strand displacement with a thymine-substituted polyamide," *Science*, 254:1497-1500 (1991).
Prashar et al., "[15] READS: A method for display of 3'-end fragments of restriction enzyme-digested cDNAs for analysis of differential gene expression", *Methods Enzymol.*, 303:258-272 (1999).
Shigekawa et al., "Extended x-ray absorption fine structure study on the cerium (IV)-induced DNA hydrolysis: implication to the roles of 4f orbitals in the catalysis", *Appl. Phys. Lett.*, 74:460-462 (1999).
Stein, "The experimental use of antisense oligonucleotides: a guide for the perplexed," *J. Clin. Invest.*, 108:641-644 (2001).
Suen et al., "Identification by UV resonance Raman spectroscopy of an imino tautomer of 5-hydroxy-2'-deoxycytidine, a powerful base analog transition mutagen with a much higher unfavored tautomer frequency than that of the natural residue 2'-deoxycytidine," *Proc. Natl. Acad. Sci. USA*, 96:4500-4505 (1999).
Sutcliffe et al., "TOGA: an automated parsing technology for analyzing expression of nearly all genes," *Proc. Natl. Acad. Sci. USA*, 97:1976-1981 (2000).
Tijsterman et al., "RNA helicase MUT-14-dependent gene silencing triggered in *C. elegans* by short antisense RNAs," *Science*, 295:694-697 (2002).
To, "Identification of differential gene expression by high throughput analysis," *Comb. Chem. High Throughput Screen.*, 3:235-241 (2000).
Trawick et al., "Inorganic mimics of ribonucleases and ribozymes: from random cleavage to sequence-specific chemistry to catalytic antisense drugs", *Chem. Rev.*, 98:939-960 (1998).

Uhlmann et al., "Antisense oligonucleotides: a new therapeutic principle", *Chem. Rev.*, 90:543-584 (1990).

Wallace, "Biological consequences of free radical-damaged DNA bases", *Free Radic. Biol. Med.*, 33:1-14 (2002).

Williams et al., "Structure and nuclease activity of simple dinuclear metal complexes: quantitative dissection of the role of metal ions", *Acc. Chem. Res.*, 32:485-493 (1999).

Zhang et al., "PowerBLAST: A new network BLAST application for interactive or automated sequence analysis and annotation," *Genome Res.*, 7:649-656 (1997).

Zhu et al., "Binuclear lanthanide complexes as catalysts for the hydrolysis of double-stranded DNA", *Inorg. Chem. Communs.*, 2:351-353 (1999).

Crooke., "Progress in Antisense Technology", Annu. Rev. Med., 55:61-95 (2004).

Hall et al., "Efficient sequence-specific cleavage of RNA using novel europium complexes conjugated to oligonucleotides", Chemistry. & Biology, 1(3):185-190 (1994).

Hamm et al., "Oligonucleotide incorporation of 8-thio-2'-deoxyguanosine", Org. Lett., 6(21):3817-3820 (2004).

Magda et al., "Site-specific hydrolysis of RNA by europium (III) texaphyrin conjugated to a synthetic oligodeoxyribonucleotide", J. Am. Chem. Soc., 116(16):7439-7440 (1994).

Manoharan, "Oligonucleotide conjugates as potential antisense drugs with improved uptake, biodistribution, targeted delivery, and mechanism of action", Antisense & Nucleic Acid Drug Development, 12:103-128 (2002).

Matsumura et al., "Lanthanide complex-oligo-DNA hybrid for sequence-selective hydrolysis of RNA", J. Chem. Soc., Chem. Commun., pp. 2019-2020 (1994).

Niittymäki e tal., "Artificial ribonucleases", Org. Biomol. Chem., 4:15-25 (2006).

Sasaki et al., "Application of unnatural oligonucleotides to chemical modification of gene expression", Current Opinion in Chemical Biology, 10:615-621 (2006).

Thiviyanathan et al., "5-hydroxyuracil can form stable base pairs with all four bases in a DNA duplex", Chem. Commun., pp. 400-402 (2005).

Wilson et al., "Building oligonucleotide therapeutics using non-natural chemistries", Current Opinion in Chemical Biology, 10:607-614 (2006).

\* cited by examiner

ANTISENSE AGENTS COMBINING STRONGLY BOUND BASE-MODIFIED OLIGONUCLEOTIDE AND ARTIFICIAL NUCLEASE

CROSS-REFERENCE TO RELATED APPLICATIONS

This application claims the benefit of U.S. Provisional Application No. 60/797,448, filed May 3, 2006, which is incorporated by reference in its entirety.

FIELD OF THE INVENTION

The invention is in the field of oligonucleotide analogs that contain specifically modified RNA or DNA bases and are bound to organic complexes of lanthanides with highly selective artificial nuclease activity.

BACKGROUND OF THE INVENTION

The use of oligonucleotides and modified oligonucleotides is of great significance in modern therapy and has been well documented (Uhlmann, et al. Antisense oligonucleotides: A new therapeutic principle. *Chemical Reviews* 1990, 90: 543-584; Crooke, et al. "Antisense Research and Applications", CRC Press (1993); Mesmaekar, et al. "Antisense oligonucleotides," *Acc. Chem. Res.* 1995, 28: 366-374; Stein. "The experimental use of antisense oligonucleotides: a guide for the perplexed." *J. Clin. Invest.* 2001, 108, 641-644.) The specific binding of antisense polynucleotides to the DNA or RNA targets can inactivate the replication, transcription, or translation of nucleic acids, thereby providing a mechanism for controlling diseases such as cancer and viral infection. The binding of an antisense oligonucleotide to a target can thus be used to alter gene expression, in a variety of circumstances, e.g., to interfere with viral life cycles, or the growth of cancerous cells.

In addition to specific binding affinity to a complementary target nucleotide sequence, antisense oligonucleotides should fulfill the requirements for therapeutic purposes, including potency, bioavailability, low toxicity, and low cost. Since oligonucleotides having a natural phosphodiester backbone are labile to nucleases and do not readily penetrate the cell membrane, researchers have attempted to make polynucleotide backbone modifications that improve nuclease resistance and cellular uptake. Therefore, it is desirable to provide polynucleotide analogs with enhanced nuclease resistance and cellular uptake, while retaining their specific interaction with nucleic acids and/or their catalytic activity.

Efforts have been directed to the development of chemical modifications of antisense oligonucleotides with higher resistance to nuclease activity (Mesmaekar, et al. "Antisense oligonucleotides." *Acc. Chem. Res.* 1995, 28: 366-374; Crooke S T. "Progress in antisense therapeutics." *Med. Res. Rev.* 1996; 16: 319-344). For instance, one approach (Wang, et al., "Sugar modified nucleosides and oligonucleotides" U.S. Pat. No. 5,681,940; Oct. 28, 1997) provides various novel sugar modified nucleosides and corresponding sugar modified oligonucleotides that have properties superior to natural RNA and DNA oligonucleotides when used for antisense, diagnostic, or other purposes. Various other modified nucleotides have been proposed as potential antisense drugs (Iyer, "Reagents and process for synthesis of oligonucleotides containing phosphorodithioate internucleoside linkages" U.S. Pat. No. 6,117,992; Sep. 12, 2000; Meyer, et al. "Oligonucleotides containing pyrazolo[3,4-d]pyrimidines for hybridization and mismatch discrimination" U.S. Pat. No. 6,127,121; Oct. 3, 2000; Froehler, et al. "Enhanced triple-helix and double-helix formation directed by oligonucleotides containing modified pyrimidines" U.S. Pat. No. 6,235,887; May 22, 2001; Cook, et al. "Substituted purines and oligonucleotide cross-linking" U.S. Pat. No. 6,232,463, May 15, 2001; Short, "Modified nucleotides and methods useful for nucleic acid sequencing" U.S. Pat. No. 6,579,704, Jun. 17, 2003).

An interesting approach to decrease the nuclease viability of oligonucleotides is via modification by inclusion of zwitterionic base forms, which electrostatically protects the phosphodiester bond (Switzer, "Antisense oligonucleotides comprising 5-aminoalkyl pyrimidine nucleotides" U.S. Pat. No. 5,596,091, Jan. 21, 1997; Switzer, "Antisense oligonucleotide containing compositions and method of forming duplexes" U.S. Pat. No. 6,031,086, Feb. 29, 2000).

It has been demonstrated by molecular modeling and accompanying experiments that certain modified purine and pyrimidine bases (e.g., 1-methyl-5-hydroxycytosine and its anionic form, 1-methyl-5-bromouracil, and 2-amino-9-methylpurine) possess zwitterionic tautomers that bind strongly with complementary native nucleic acid bases (Suen, et al. "Identification by UV resonance Raman spectroscopy of an imino tautomer of 5-hydroxy-2'-deoxycytidine, a powerful base analog transition mutagen with a much higher unfavored tautomer frequency than that of the natural residue 2'-deoxycytidine." *Proc. Natl. Acad. Sci. USA* 1999, 96: 4500-4505. Karelson, et al. "Quantum-Chemical Modeling of the Tautomeric Equilibria of Modified Anionic Nucleic Acid Bases," *ARKIVOC*, 2001, 3, 51-62.

There has also been great interest in designing organic-metal complexes that are capable of catalytically hydrolyzing nucleic acids. (Morrow, "Artificial Ribonucleases," *Adv. Inorg. Biochem.*, 1994, 9:41-74; Magda, "Metal Complex Conjugates of Antisense DNA Which Display Ribozyme-Like Activity," *J. Am. Chem. Soc.* 1997, 119:6947-6948; Komiyama, "Progress towards synthetic enzymes for phosphoester hydrolysis," *Current Opinion in Chemical Biology*, 1998, 2:751-757; Hegg, "Toward the development of metal-based synthetic nucleases and peptidases: a rationale and progress report in applying the principles of coordination chemistry," *Coord. Chem. Revs.* 1998, 173: 133-165; Trawick et al. "Inorganic Mimics of Ribonucleases and Ribozymes: From Random Cleavage to Sequence-Specific Chemistry to Catalytic Antisense Drugs," *Chem. Rev.* 1998, 98: 939-960.) The complexes of certain lanthanides (e.g., lanthanum, europium, cerium, gadolinium) possess comparable or even higher phosphodiesterase activity than the native enzymes (Bing Zhua, et al., "Binuclear lanthanide complexes as catalysts for the hydrolysis of double-stranded DNA," *Inorg. Chem. Communs.*, 1999, 2: 351-353; Williams, et al., "Structure and Nuclease Activity of Simple Dinuclear Metal Complexes: Quantitative Dissection of the Role of Metal Ions," *Acc. Chem. Res.* 1999, 32: 485-493; Häner et al. "Development of Artificial Ribonucleases Using Macrocyclic Lanthanide Complexes," *Chimia* 2000, 54:569-573; Kuzuya, et al., "Conjugation of Various Acridines to DNA for Site-Selective RNA Scission by Lanthanide Ion," *Bioconjugate Chem.* 2002, 13: 365-369; Canaple, et al., "Artificial Ribonucleases: Efficient and Specific in Vitro Cleavage of Human c-raf-1 RNA," *Bioconjugate Chem.* 2002, 13:945-951; Shigekawa et al., "Extended x-ray absorption fine structure study on the cerium(IV)-induced DNA hydrolysis: Implication to the roles of 4 f orbitals in the catalysis" *Appl. Phys. Lett.* 1999, 74: 460-462.)

One potential means of providing synthetic RNA transesterification catalysts may be via the creation of more potent antisense oligonucleotides through the attachment of a catalytic cleaving group, which would render them efficient and selective mutagenic and antiviral agents. (Hall, et al. "Efficient sequence-specific cleavage of RNA using novel europium complexes conjugated to oligonucleotides", *Chemistry & Biology*, 1994, 1: 185-190; Komiyama, "Sequence-specific and hydrolytic scission of DNA and RNA by lanthanide complex-oligoDNA hybrids", *J. Biochem.*, 1995, 118:665-670; Hall et al. "Towards artificial ribonucleases: The sequence-specific cleavage of RNA in a duplex", *Nucl. Acid Res.*, 1996, 24: 3522-3526; Hall et al. "Sequence-specific cleavage of RNA using macrocyclic lanthanide complexes conjugated to oligonucleotides: A structure activity study," *Nucleosides & Nucleotides*, 1997, 16: 1357-1368; Häner et al. "The sequence-specific cleavage of RNA by artificial chemical ribonucleases," *Antisense and nucleic acid drug development*, 1997, 7: 423-430; Baker et al. "Oligonucleotide-europium complex conjugate designed to cleave the 5' cap structure of the ICAM-1 transcript potentiates antisense activity in cells," *Nucl. Acid Res.*, 1999, 17:1547-1551; Haner et al, "Functional terpyridine-metal complexes, a process for the preparation thereof and oligonucleotide conjugates with terpyridine-metal complexes" U.S. Pat. No. 5,925,744, Jul. 20, 1999; Morrow, "Metal complexes for promoting catalytic cleavage of RNA by transesterification" U.S. Pat. No. 5,684,149; Nov. 4, 1997) Artificial enzymes for selective scission of RNA at one or two designated sites have been prepared by combining a lanthanide(III) ion with an oligonucleotide bearing one or two acridine groups. (Kuzuya et al. "Conjugation of Various Acridines to DNA for Site-Selective RNA Scission by Lanthanide Ion," *Bioconjugate Chem.* 2002, 13: 365-369; Kuzuya et al. "Selective activation of two sites in RNA by acridine-bearing oligonucleotides for clipping of designated RNA fragments," *J. Am. Chem. Soc.*, 2004, 126: 1430-1436.)

SUMMARY OF THE INVENTION

The present invention relates to compounds having oligonucleotides wherein the oligonucleotides comprise modified nucleobases and/or chelating moieties, which increase their binding ability to complementary nucleic acids and can impart phosphodiesterase activity. Depending on the nature of the number of modified nucleobases in the oligonucleotide portion of the disclosed compounds, the binding ability of the compound to a complementary target nucleic acid can be increased up to $10^3$-$10^9$ times, compared to a typical complementary oligonucleotide. Such increases in binding can allow for lower concentrations of the agents to be employed for industrial, prophylactic, therapeutic, or other purposes. Additionally or alternatively, the catalytic activity of the compounds of the present invention modified with a chelating group capable of complexing to a metal ion can allow for lower effective concentrations of the compounds (as compared to prior antisense therapy compounds), as the compound can complex to a complementary strand, catalyze phosphodiester bond cleavage, and repeat with another complementary strand.

The materials of the invention are useful for all variety of procedures for which antisense nucleic acids are employed or might be employed in the future, including, but not limited to, diagnosis, therapy, and modulation of gene expression of a host or a pathogen.

In view of the exquisite binding power, the materials of the invention are also useful as detection probes for detecting and/or quantifying target nucleic acids.

Therefore, one aspect of the invention is compounds having a chelating moiety and an oligonucleotide of about 5 to about 150 nucleobases, wherein the oligonucletide further comprises at least one modified nucleobase, such as a zwitterionic tautomer, ionic tautomer, mercaptonucleobases, or hydroxynucleobase. In a preferred embodiment, the oligonucleotide has about 10 to about 100 nucleobases, more preferred, about 10 to about 50 nucleobases, and most preferred, about 20 to about 30 nucleobases. In some cases, the oligonucleotide has at least 2 modified nucleobases. In preferred embodiments, the modified nucleobases are mercaptonucleobases and/or hydroxynucleobases. In certain embodiments, the hydroxynucleobases are from about 10% to about 20% of the total number of nucleobases in the compound. In preferred embodiments, the hydroxynucleobase is 5-hydroxycytosine, 5-hydroxyuracil, 8-hydroxyadenine or 8-hydroxyguanine and/or the mercaptonucleobase is 5-mercaptocytosine, 5-mercaptouracil, 8-mercaptoguanine, or 8-mercaptoadenine.

As used herein, a chelating moiety is a moiety of a compound that is capable of complexing to an ion of a metal. In preferred embodiments, the metal is a lanthanide, and in more preferred embodiments, the metal is selected from the group consisting of lanthanum, cerium, praseodymium, neodymium, promethium, samarium, europium, gadolinium, terbium, dysprosium, holmium, erbium, thulium, ytterbium, and lutetium. Particularly preferred metals are europium and lanthanum. Preferred chelating moieties are ones having a formula selected from:

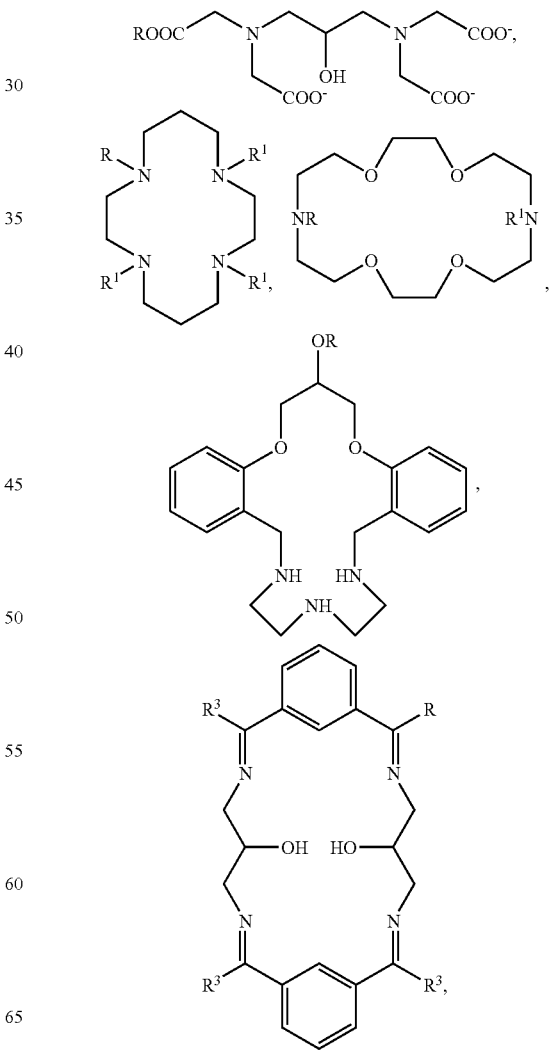

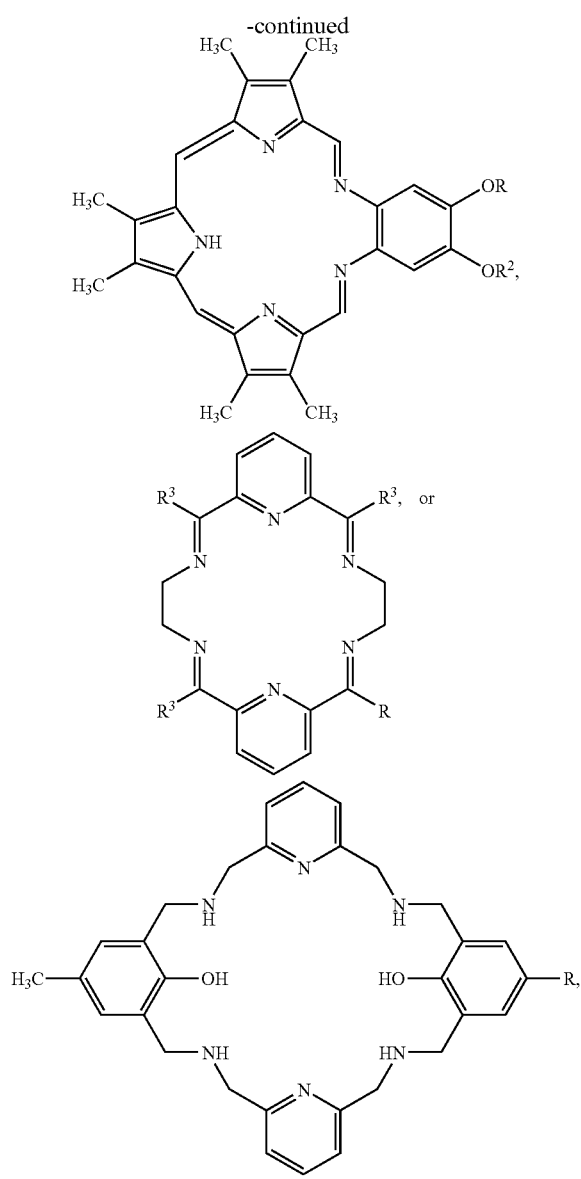

wherein R is the oligonucleotide portion of the compound. $R^1$ and $R^3$ can be hydrogen, $C_{1-8}$ alkane, $C_{2-8}$ alkene, $C_{2-8}$ alkyne, acyl$C_{1-8}$alkane, cycloalkyl, heterocycloalkyl, aryl, heteroaryl, $C_{1-8}$alkylaryl, or $C_{1-8}$alkylheteroaryl. $R^2$ can be $C_{1-8}$ alkyl, $C_{2-8}$ alkene, $C_{2-8}$ alkyne, aryl, heteroaryl, $C_{1-8}$alkylaryl, $C_{1-8}$alkylheteroaryl, or acyl$C_{1-8}$alkane. In one specific embodiment, the chelating moiety is:

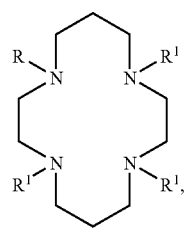

where $R^1$ are each 2,2,2-trifluoroacetyl, and R is the oligonucleotide.

An other aspect of the invention is a composition comprising a compound as disclosed herein and a pharmaceutically acceptable carrier. In some embodiments, the composition further comprises a delivery vehicle, such as a liposome.

Yet another aspect of the invention is a method of inhibiting translation of a target nucleic acid with a compound as described herein. For instance, such a method comprises contacting the target nucleic acid with a compound of the present invention under conditions which permit hybridization of the compound to the target nucleic acid, wherein the hybridized compound inhibits translation of the target nucleic acid. In some cases, the compound cleaves a bond of the target nucleic acid. In certain embodiments, the target nucleic acid is mRNA. In some embodiments, the target nucleic acid is in an organism and the contacting comprises administering to the organism a composition comprising the compound of the present invention and a pharmaceutically acceptable carrier. Alternatively, in other embodiments, the contacting comprises mixing the compound of the present invention with a biological sample from the organism which comprises the target nucleic acid. In some cases, the organism is a human or animal subject. In a specific embodiment, the human or animal subject suffers from a viral infection, bacterial infection, microbial infection, fungal infection, or cancer.

Still another aspect of the invention is a method of inhibiting translation of a nucleic acid in an organism, comprising predicting or determining a nucleic acid sequence of a target nucleic acid in the organism, and administering to the organism a composition comprising a compound of the present invention and a pharmaceutically acceptable carrier. In some cases, the composition further comprises a delivery vehicle, such as a liposome. The compound administered in the composition comprises a nucleotide sequence that is sufficiently complementary to the nucleotide sequence of the target nucleic acid to hybridize thereto in the organism under conditions sufficient to permit such hybridization, thereby inhibiting translation of the nucleic acid in the organism. In some cases, the nucleotide sequence of the compound is fully complementary to all or a portion of the sequence of the target nucleic acid.

Yet another aspect of the present invention is a method of making a compound to inhibit translation of a target nucleic acid under conditions sufficient to permit hybridization, comprising (a) determining a nucleotide sequence of a target nucleic acid; (b) synthesizing a compound that comprises a chelating moiety attached to an oligonucleotide comprising an oligonucleotide sequence that is complementary to at least part of the nucleotide sequence of the target nucleic acid and from 5 to 150 nucleobases wherein at least one nucleobase is a hydroxynucleobase selected from 5-hydroxycytosine, 5-hydroxyuracil, 8-hydroxyadenine and 8-hydroxyguanine; and (c) mixing the compound with a ion of a metal selected from lanthanum, cerium, praseodymium, neodymium, promethium, samarium, europium, gadolinium, terbium, dysprosium, holmium, erbium, thulium, ytterbium, and lutetium. In some embodiments, the chelating moiety has a formula

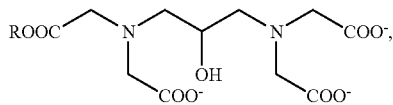

-continued

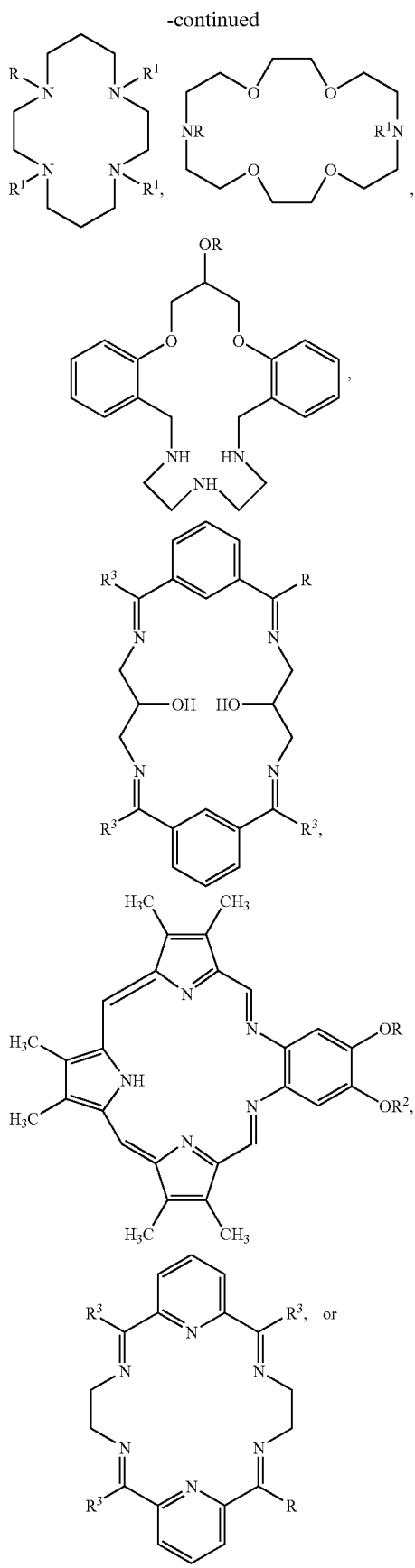

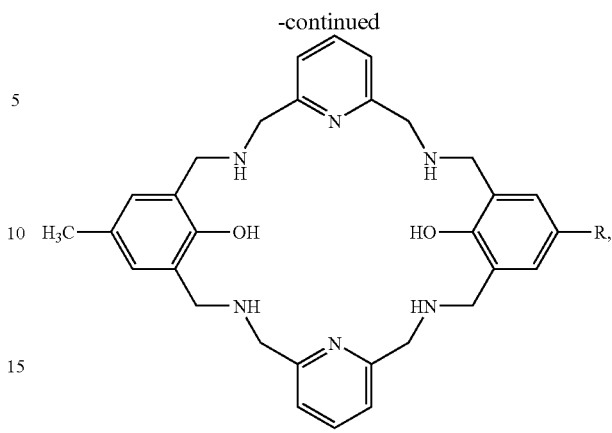

wherein R is the oligonucleotide portion of the compound. $R^1$ and $R^3$ can be hydrogen, $C_{1-8}$ alkane, $C_{2-8}$ alkene, $C_{2-8}$ alkyne, acyl$C_{1-8}$alkane, cycloalkyl, heterocycloalkyl, aryl, heteroaryl, $C_{1-8}$alkylaryl, or $C_{1-8}$alkylheteroaryl. $R^2$ can be $C_{1-8}$ alkyl, $C_{2-8}$ alkene, $C_{2-8}$ alkyne, aryl, heteroaryl, $C_{1-8}$alkylaryl, $C_{1-8}$alkylheteroaryl, or acyl$C_{1-8}$alkane. In a specific embodiment, the conditions sufficient to permit hybridization are human physiological conditions.

In addition to the foregoing, the invention includes, as an additional aspect, all embodiments of the invention narrower in scope in any way than the variations specifically mentioned above. For example, although aspects of the invention may have been described by reference to a genus or a range of values for brevity, it should be understood that each member of the genus and each value or sub-range within the range is intended as an aspect of the invention. Likewise, various aspects and features of the invention can be combined, creating additional aspects which are intended to be within the scope of the invention. Although the applicant(s) invented the full scope of the claims appended hereto, the claims appended hereto are not intended to encompass within their scope the prior art work of others. Therefore, in the event that statutory prior art within the scope of a claim is brought to the attention of the applicants by a Patent Office or other entity or individual, the applicant(s) reserve the right to exercise amendment rights under applicable patent laws to redefine the subject matter of such a claim to specifically exclude such statutory prior art or obvious variations of statutory prior art from the scope of such a claim. Variations of the invention defined by such amended claims also are intended as aspects of the invention.

DETAILED DESCRIPTION OF THE PREFERRED EMBODIMENTS

Figure 1:
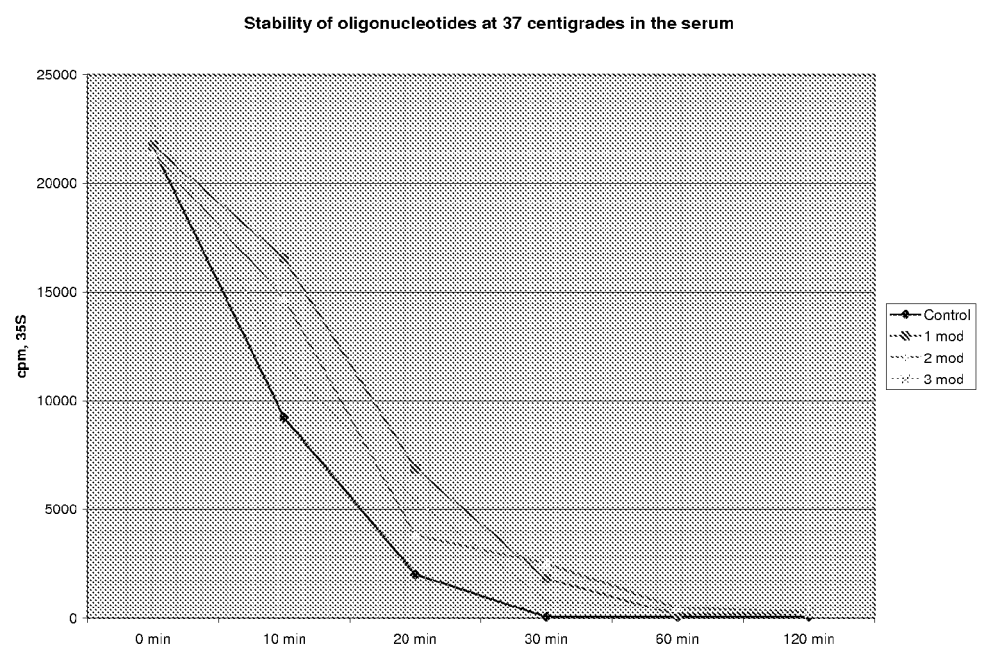
FIG. 1 is a graph depicting stability in serum at 37° C. of oligonucleotides having 0, 1, 2, or 3 hydroxy-guanine nucleic acids incorporated.

The current invention provides novel compounds comprises a chelating moiety and an oligonucleotide having properties for use in antisense, diagnostic, and other methods employing oligonucleotides. The compounds of the invention include antisense oligonucleotides having (a) one or more modified nucleobases having high binding efficiency to natural nucleobases and (b) one or more chelating moieties. These compounds can hydrolyze phosphodiester bonds of oligonucleotides, RNA, and/or DNA, and are useful in antisense therapies.

In the context of this invention, the term "oligonucleotide" refers to an oligomer or polymer of ribonucleic acid (RNA) or deoxyribonucleic acid (DNA) or mimetics, chimeras, analogs and homologs thereof. This term includes oligonucleotides composed of naturally occurring nucleobases, sugars and covalent internucleoside (backbone) linkages as well as oligonucleotides having non-naturally occurring portions which function in a similar manner as naturally occurring oligonucleotides when, e.g., hybridizing to target nucleic acids or interacting with complementary oligonucleotides. Such modified or substituted oligonucleotides are often preferred over native forms because of desirable properties such as, for example, enhanced cellular uptake, enhanced affinity for a target nucleic acid and increased stability in the presence of nucleases.

The efficiency of binding of compounds of the present invention to biological counterparts (e.g., oligonucleotide, RNA, or DNA) is attained via incorporation of modified nucleobases or other analogs having zwitterionic or ionic tautomers. Compounds of the present invention have at least one nucleobase having modified nucleobases or other analogs having zwitterionic or ionic tautomers. In preferred embodiments, the modified nucleobase is a hydroxynucleobase selected from 5-hydroxycytosine, 5-hydroxyuracil, 8-hydroxyadenine and 8-hydroxyguanine or a mercaptonucleobase selected from 5-mercaptocytosine, 5-mercaptouracil, 8-mercaptoguanine, and 8-mercaptoadenine.

In one embodiment, an oligonucleotide comprises one or more tautomeric forms of the 5-hydroxyuracil anion (1) having the formulae (Scheme 1):

Scheme 1

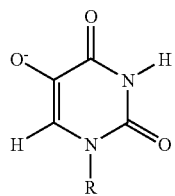

1a

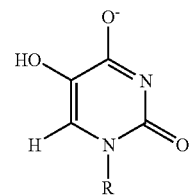

1b

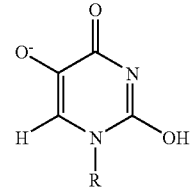

1c

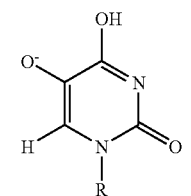

1d where R relates to the rest compound of the present invention. The results of semi-empirical AM1 and PM3 and ab initio SCF and DFT (BLYP/6-31+G(d)) calculations indicate that the most stable tautomer of the anion of 1-methyl-5-hydroxyuracil in the solution is the form with the intact OH-group at the 5-position (1b). Because of the lack of the hydrogen atom at N3 position, the normal pairing of the 1-methyl-5-hydroxyuracil anion tautomer 1b with adenine is incapacitated. However, this tautomeric form of 1-methyl-5-hydroxyuracil anion (1b) produces a strongly bonded complex with guanine as the reverse Watson-Crick pair (Scheme 2).

Scheme 2

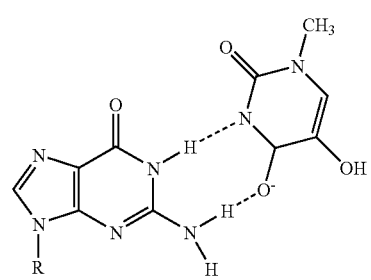

Because of the substantial negative charge on the C4 carbonyl (closeness to the oxy-anion) of the 1-methyl-5-hydroxyuracil anion 1b, this pair will be substantially more strongly bonded than the native guanine-cytosine pair. The calculations reveal that the reverse Watson-Crick pair between guanine and 1-methyl-5-hydroxyuracil anion is by 2 to 4 kcal/mol more stable than the normal guanine-cytosine pair.

In another embodiment, the compounds of the present invention include the hydroxybase 5-hydroxycytosine (2). The tautomeric forms of the 5-hydroxycytosine (2) anion are given on Scheme 3, where R denotes again the rest of the compound.

Scheme 3

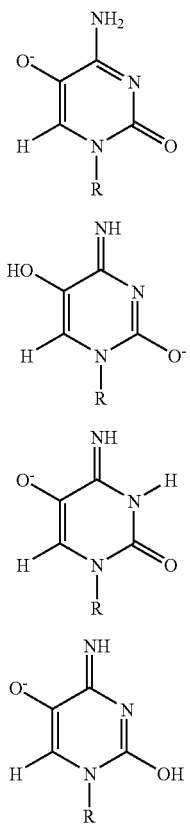

2a

2b

2c

2d

In the case of the 1-methyl-5-hydroxycytosine anion, the structure 2b is the most stable tautomeric form in the solution. This N—H form of the anion has substantial negative charge on the C2 carbonyl oxygen atom. As a result, the respective pair with the guanine (Scheme 4) is significantly more strongly bonded than the normal guanine-cytosine pair.

Scheme 4

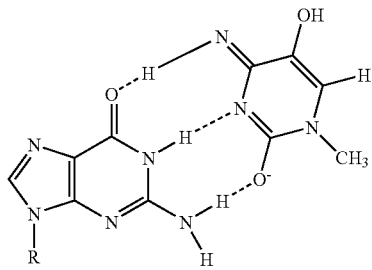

The AM1 SCRF calculations predict that the abnormal guanine—tautomer 2b pair is by 5.42 kcal/mol more stable than the normal guanine—cytosine Watson-Crick pair. The respective calculated difference using PM3 parameterization is even larger, roughly 10.21 kcal/mol. Consequently, such strong bonding may substantially affect the normal DNA replication process and lead to the mutations or even cell termination. This is in accordance with the experimental observation of 5-hydroxycytosine, similarly to 5-hydroxyuracil being an extremely strong mutagenic agent (Wallace. "Biological consequences of free radical-damaged DNA bases," *Free Radical Biology and Medicine,* 2002, 33:1-14). However, within the present embodiment, the very low concentration of this component guarantees only the strong bonding of specific title compounds, with negligible non-specific bonding to random complementary bases in biological counterparts (DNA, RNA).

In another embodiment of the present invention, the hydroxybase is a tautomeric form of the 8-hydroxyadenine and its anion (3). The respective tautomeric forms of this anion are given in Scheme 5, where R denotes again the rest of the compound.

Scheme 5

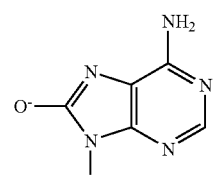

3a

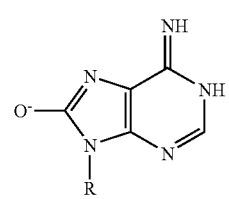

3b

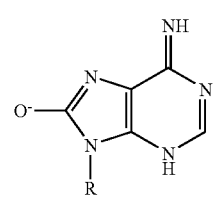

3c

In the case of anion of 9-methyl-8-hydroxyadenine, the most stable tautomeric form is the ionized 8-hydroxyl form 3a. In this case, the normal bonding with uracil is only slightly affected. However, the calculations indicate that the most stable tautomer in the solution of the neutral 9-methyl-8-hydroxyadenine is the zwitterionic form 4, presented on Scheme 6.

Scheme 6

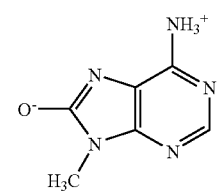

4

Because of the positive ionic charge on the ammonium-group this tautomer forms very strong hydrogen bonds with uracil. The 9-methyl-8-hydroxyadenine zwitterionic tautomer 4 pair with uracil was calculated to be by 5.16 kcal/mol (AM1 MCa SCRF) to 8.41 kcal/mol (PM3 MCa SCRF) more stable than the normal adenine-uracil pair (cf. Scheme 7).

Scheme 7

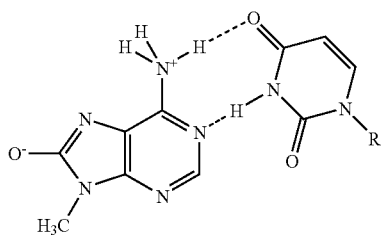

This is again in accordance with the very high mutagenic activity of the 8-hydroxyadenine (Wallace. "Biological consequences of free radical-damaged DNA bases," *Free Radical Biology and Medicine,* 2002, 33:1-14). However, the expected increased bonding allows to decrease the concentration of compounds of the present invention by up to 5 orders of magnitude in comparison to compounds having natural nucleobases only.

Another embodiment of the invention provides compounds of the present invention modified by tautomeric forms of the 8-hydroxyguanine and its anion (5). The respective tautomeric forms of this anion are given in Scheme 8, where R denotes again the rest of the compound.

Scheme 8

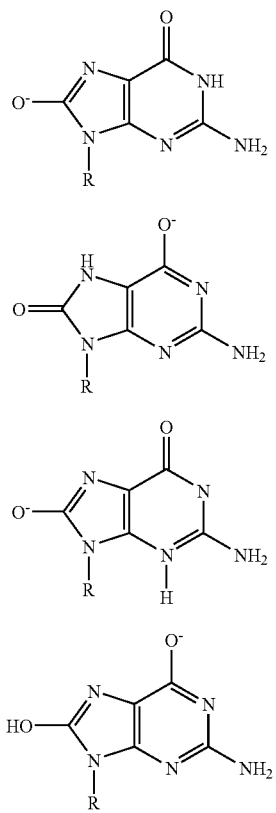

In the case of anion of 9-methyl-8-hydroxyguanine, the most stable tautomeric form is the ionized 8-hydroxyl form 5a. which bounds energetically similarly to the normal base pairing. However, the most stable tautomer in the solution of the neutral 9-methyl-8-hydroxyguanine, the zwitterionic form 6 presented on Scheme 9, has very strong bonding with cytosine.

Scheme 9

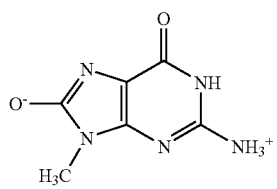

The 9-methyl-8-hydroxyguanine zwitterionic tautomer 6 pair with cytosine was predicted to be more stable than the normal guanine-cytosine pair by 7.22 kcal/mol (AM1 MCa SCRF) to 8.17 kcal/mol (PM3 MCa SCRF). The structure of such pair is given on Scheme 10.

Scheme 10

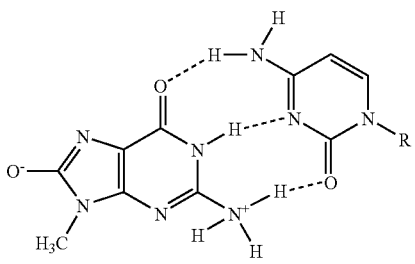

As used herein, each of the hydroxynucleobases is considered complementary to a nucleobase when it stably hydrogen bonds to the opposite nucleobase. Therefore, in some cases, 5-hydroxyuracil is complementary to adenine, 5-hydroxycytosine is complementary to guanine, 8-hydryoxyandenine is complementary to uracil and/or thymine, and 8-hydroxyguanine is complementary to cytosine. Other stable hydrogen bonding of a hydroxynucleobase with a nucleobase of a target nucleic acid can occur, and, therefore, a hydroxynucleobase is considered complementary to the nucleobases of the target nucleic acid to which stable hydrogen bonding occurs.

The acidic tautomeric group in the modified nucleobases can be any other acidic group such as the —SH, —COOH, —SO$_3$H, etc. In an exemplary embodiment, there is a substantial difference in the stabilization of the complexes between the guanine and cytosine (7a), and the zwitterionic form of 8-mercaptoguanine and cytosine (7b), respectively.

Scheme 11

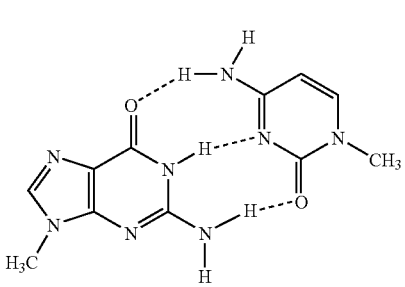

-continued

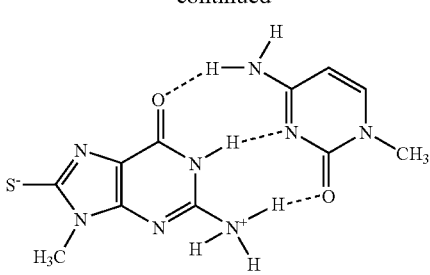

7b

The DFT (B3LYP) calculation with 6-31G**+ basis set using Jaguar (Jaguar 6.5, Schrodinger, LLC, New York, N.Y., 2005) gives the following complex stabilization energy values: −0.038376 a.u. for 7a vs. −0.073251a.u. for 7b, thus referring to the existence of much stronger bonding in the latter. Consequently, the presence of 8-mercaptoguanine and equivalent tautomeric compounds in nucleotides, oligonucleotides and nucleic acids will enhance the stability of RNA-RNA, RNA-DNA, DNA-DNA, RNA-protein and DNA-protein hydrogen-bonded complexes. The stability of these complexes has utility for RNAi diagnostics, antisense nucleotide therapies, the nucleic acid microarray diagnostics and for various laboratory diagnostic and clinical methods utilizing them.

In Table 1, the AM1 SCRF ($\epsilon$80) calculated heats of formation $\Delta H_f^o$ and the relative tautomeric equilibrium constants $\Delta pK_T$ for the above-discussed compounds are given.

TABLE 1

| Tautomer | $\Delta H_f^o$ (kcal/mol) | $\Delta pK_T$ |
|---|---|---|
| 1a | −170.04 | 2.37 |
| 1b | −173.31 | (0) |
| 1c | −160.90 | 9.00 |
| 1d | −155.49 | 12.92 |
| 2a | −104.41 | 1.02 |
| 2b | −105.82 | (0) |
| 2c | −105.38 | 0.32 |
| 2d | −92.93 | 9.35 |
| 3a | −26.96 | (0) |
| 3b | −13.98 | 9.42 |
| 3c | −14.09 | 9.33 |
| 5a | −74.99 | (0) |
| 5b | −42.92 | 23.26 |
| 5c | −39.18 | 25.97 |
| 5d | −71.76 | 2.34 |

The number of hydroxynucleobases in a given compound of the present invention is at least one, but no more than 20% of the total number of nucleobases of the oligonucleotide portion of the compound. More than 20% hydroxynucleobases can lead to instability of the compound and decreased binding to a target nucleic acid. Preferred numbers of hydroxynucleobases are from about 10% to about 20% of the total number of nucleobases. In cases where more than one hydroxynucleobase is present in the compounds of the present invention, the hydroxynucleobases may be the same or different.

The compounds in accordance with this invention preferably comprise from about 5 to about 150 nucleobases (i.e. from about 5 to about 150 linked nucleosides). One of ordinary skill in the art will appreciate that the invention embodies compounds of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, and 150 nucleobases in length.

In one preferred embodiment, the compounds of the invention are 10 to 100 nucleobases in length. One having ordinary skill in the art will appreciate that this embodies compounds of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nucleobases in length.

In another preferred embodiment, the compounds of the invention are 10 to 50 nucleobases in length. One having ordinary skill in the art will appreciate that this embodies compounds of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleobases in length.

In another preferred embodiment, the compounds of the invention are 20 to 30 nucleobases in length. One having ordinary skill in the art will appreciate that this embodies compounds of 20, 21, 22, 23, 24, 25, 26, 27, 28, 29, or 30 nucleobases in length.

Particularly preferred compounds are oligonucleotides from about 10 to about 50 nucleobases, even more preferably those comprising from about 20 to about 30 nucleobases.

The compound of the present invention further comprise a chelating moiety. Chelating moieties function as metal ligands. They can stably chelate a metal ion. Certain metal-ligand complexes have been shown effective in cleaving phosphodiester bonds. In incorporating a chelating moiety into an oligonucleotide capable of antisense activity, the efficacy of the oligonucleotide in inhibiting a target nucleic acid increases, due to its ability to degrade or cleave one or more phosphodiester bonds of the target nucleic acid. Therefore, the compounds of the present invention further comprise chelating moieties capable of chelating a metal ion. In preferred embodiments, the metal ion is lanthanum, cerium, praseodymium, neodymium, promethium, samarium, europium, gadolinium, terbium, dysprosium, holmium, erbium, thulium, ytterbium, and lutetium. Particularly preferred are ions of europium or lanthanum. Ions of the metals can be any stable ion, such as +1, +2, +3, +4, or +5. Preferred ions are La(III), Eu(III), Ho(III), and Ce(IV).

Contemplated chelating moieties include those represented by formulas as outlined in Scheme 12.

Scheme 12

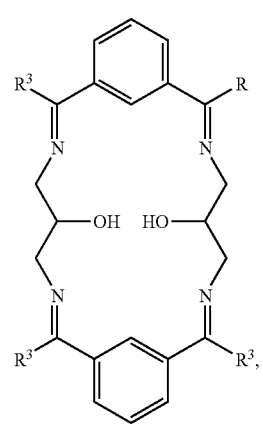

-continued

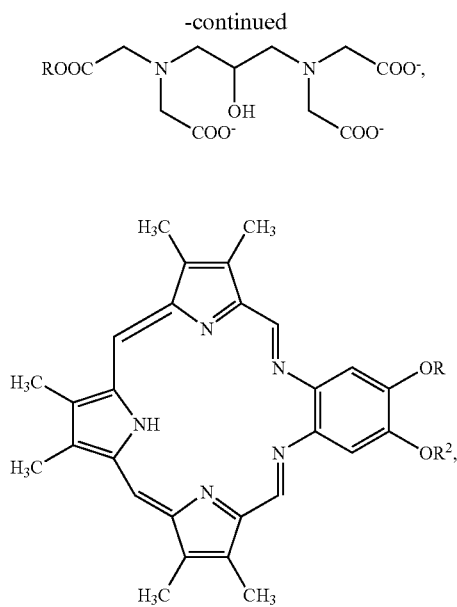

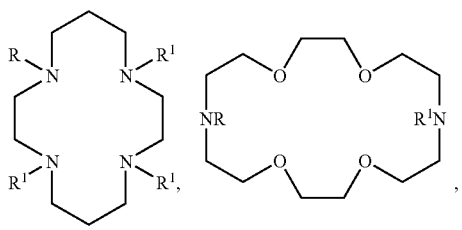

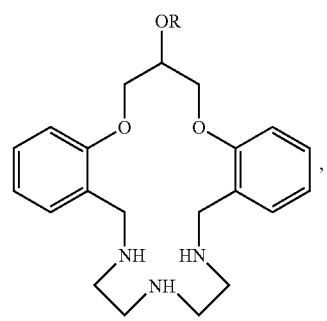

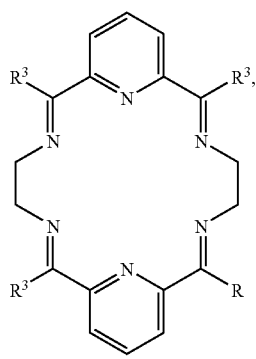

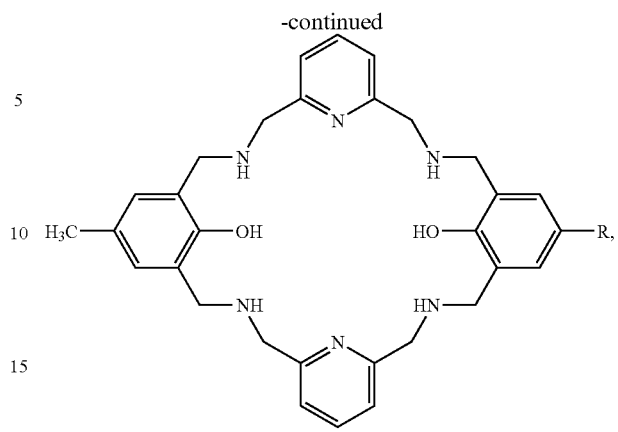

where R is the rest of the oligonucleotide;

$R^1$ is selected from hydrogen, $C_{1-8}$ alkane, $C_{2-8}$ alkene, $C_{2-8}$ alkyne, acyl$C_{1-8}$alkane, cycloalkyl, heterocycloalkyl, aryl, heteroaryl, $C_{1-8}$alkylaryl, and $C_{1-8}$alkylheteroaryl $R^2$ is independently selected from $C_{1-8}$ alkyl, $C_{2-8}$ alkene, $C_{2-8}$ alkyne, aryl, heteroaryl, $C_{1-8}$alkylaryl, $C_{1-8}$alkylheteroaryl, and acyl$C_{1-8}$alkane, and $R^3$ is independently selected from the group consisting of hydrogen, $C_{1-8}$ alkane, $C_{2-8}$ alkene, $C_{2-8}$ alkyne, acyl$C_{1-8}$alkane, cycloalkyl, heterocycloalkyl, aryl, heteroaryl, $C_{1-8}$alkylaryl, and $C_{1-8}$alkylheteroaryl.

The term "alkyl" includes straight chained and branched hydrocarbon groups containing the indicated number of carbon atoms, typically methyl, ethyl, and straight chain and branched propyl and butyl groups. The hydrocarbon group can contain up to 16 carbon atoms. The term "alkyl" includes "bridged alkyl," e.g., a $C_6$-$C_{16}$ bicyclic or polycyclic hydrocarbon group, for example, norbornyl, adamantyl, bicyclo[2.2.2]octyl, bicyclo[2.2.1]heptyl, bicyclo[3.2.1]octyl, and decahydronaphthyl. The term "alkyl" also encompasses alkyl groups which are optionally substituted with, e.g., one or more halogen atoms, one or more hydroxyl groups, or one or more thiol groups. The term "cycloalkyl" is defined as a cyclic $C_3$-$C_8$ hydrocarbon group, e.g., cyclopropyl, cyclobutyl, cyclohexyl, and cyclopentyl. "Heterocycloalkyl" is defined similar to cycloalkyl, except at least one heteroatom is present in the cyclic structure. Suitable heteroatoms include N, S, and O.

The terms "alkenyl" and "alkynyl" are defined identically as "alkyl," except for containing a carbon-carbon double bond or carbon-carbon triple bond, respectively. "Cycloalkenyl" is defined similarly to cycloalkyl, except a carbon-carbon double bond is present in the ring.

The term "alkylene" refers to an alkyl group having a substituent. For example, the term "$C_{1-3}$alkylenearyl" refers to an alkyl group containing one to three carbon atoms, and substituted with an aryl group.

The term "halo" or "halogen" is defined herein to include fluorine, bromine, chlorine, and iodine.

The term "aryl," alone or in combination, is defined herein as a monocyclic or polycyclic aromatic group, preferably a monocyclic or bicyclic aromatic group, e.g., phenyl or naphthyl. Unless otherwise indicated, an "aryl" group can be unsubstituted or substituted, for example, with one or more, and in particular one to three, halo, alkyl, hydroxy, C(=O) OR, hydroxyalkyl, alkoxy, alkoxyalkyl, haloalkyl, haloalkoxy, cyano, nitro, amino, alkylamino, acylamino, alkylthio, alkylsulfinyl, and alkylsulfonyl. Exemplary aryl groups include phenyl, naphthyl, tetrahydronaphthyl, 2-chlorophenyl, 3-chlorophenyl, 4-chlorophenyl, 2-methylphenyl, 4-methoxyphenyl, 3-trifluoromethylphenyl, 4-nitrophenyl, and the like. The terms "arylC$_{1-3}$alkyl" and "heteroarylC$_{1-3}$alkyl" are defined as an aryl or heteroaryl group having a C$_{1-3}$alkyl substituent.

The term "heteroaryl" is defined herein as a monocyclic or bicyclic ring system containing one or two aromatic rings and containing at least one nitrogen, oxygen, or sulfur atom in an aromatic ring, and which can be unsubstituted or substituted, for example, with one or more, and in particular one to three, substituents, like halo, alkyl, hydroxy, hydroxyalkyl, alkoxy, alkoxyalkyl, haloalkyl, nitro, amino, alkylamino, acylamino, alkylthio, alkylsulfinyl, and alkylsulfonyl. Examples of heteroaryl groups include thienyl, furyl, pyridyl, oxazolyl, quinolyl, isoquinolyl, indolyl, triazolyl, isothiazolyl, isoxazolyl, imidizolyl, benzothiazolyl, pyrazinyl, pyrimidinyl, thiazolyl, and thiadiazolyl.

The term "Het" is defined as monocyclic, bicyclic, and tricyclic groups containing one or more heteroatoms selected from the group consisting of oxygen, nitrogen, and sulfur. A "Het" group also can contain an oxo group (=O) attached to the ring. Nonlimiting examples of Het groups include 1,3-dioxolanyl, 2-pyrazolinyl, pyrazolidinyl, pyrrolidinyl, piperazinyl, a pyrrolinyl, 2H-pyranyl, 4H-pyranyl, morpholinyl, thiopholinyl, piperidinyl, 1,4-dithianyl, and 1,4-dioxane.

The term "hydroxy" is defined as —OH.

The term "alkoxy" is defined as —OR, wherein R is alkyl.

The term "alkoxyalkyl" is defined as an alkyl group wherein a hydrogen has been replaced by an alkoxy group. The term "(alkylthio)alkyl" is defined similarly as alkoxyalkyl, except a sulfur atom, rather than an oxygen atom, is present.

The term "hydroxyalkyl" is defined as a hydroxy group appended to an alkyl group.

The term "amino" is defined as —NH$_2$, and the term "alkylamino" is defined as —NR$_2$, wherein at least one R is alkyl and the second R is alkyl or hydrogen.

The term "acylamino" is defined as RC(=O)N—, wherein R is alkyl or aryl.

The term "alkylthio" is defined as —SR, wherein R is alkyl.

The term "alkylsulfinyl" is defined as RSO$_2$—, wherein R is alkyl.

The term "alkylsulfonyl" is defined as RSO$_3$—, wherein R is alkyl.

The term "nitro" is defined as —NO$_2$.

The term "trifluoromethyl" is defined as —CF$_3$.

The term "trifluoromethoxy" is defined as —OCF$_3$.

The term "cyano" is defined as —CN.

The calculated nuclease efficiency of a compound of the present invention comprising a chelating moiety complexed to a metal ion increases, depending on the nature of the number of modified nucleobases, up to $10^3$-$10^9$ times in comparison to naturally-occurring nucleases, allowing a corresponding lowering of the effective concentration, and keeping at the same time high specificity of the compound.

The disclosed chelating moieties can be prepared using known techniques (see, e.g., Cowan, *Curr. Opin. Chem. Biol.*, 5:634-642 (2001) and Franklin, *Curr. Opin. Chem. Biol.*, 5:201-208 (2001)). They can additionally and alternatively be synthesized using readily available materials and known protecting group chemistries, such as those disclosed in, e.g., Wuts et al., *Greene's Protective Groups in Organic Synthesis*, 4$^{th}$ ed. (Hoboken, N.J.: Wiley-Interscience) 2007.

Further Modifications of Compounds of the Invention

Other modifications of compounds of this invention are also contemplated. While oligonucleotides are a preferred form of the compounds of this invention, the present invention comprehends other families of compounds as well, including but not limited to oligonucleotide analogs and mimetics such as those described herein.

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn, the respective ends of this linear polymeric compound can be further joined to form a circular compound, however, linear compounds are generally preferred. In addition, linear compounds may have internal nucleobase complementarity and may therefore fold in a manner as to produce a fully or partially double-stranded compound. Within oligonucleotides, the phosphate groups are commonly referred to as forming the internucleoside backbone of the oligonucleotide. The normal linkage or backbone of RNA and DNA is a 3' to 5' phosphodiester linkage.

Modified Internucleoside Linkages (Backbones)

Specific examples of contemplated antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Contemplated modified oligonucleotide backbones containing a phosphorus atom therein include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Contemplated oligonucleotides having inverted polarity comprise a single 3' to 3' linkage at the 3'-most internucleotide linkage i.e. a single inverted nucleoside residue which may be a basic (the nucleobase is missing or has a hydroxyl group in place thereof). Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253;

5,571,799; 5,587,361; 5,194,599; 5,565,555; 5,527,899; 5,721,218; 5,672,697 and 5,625,050, each of which is herein incorporated by reference.

Contemplated modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, each of which is herein incorporated by reference.

Modified Sugar and Internucleoside Linkages-Mimetics

In other contemplated oligonucleotide mimetics, both the sugar and the internucleoside linkage (i.e. the backbone), of the nucleotide units are replaced with novel groups. The nucleobase units are maintained for hybridization with an appropriate target nucleic acid. One such compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., *Science*, 1991, 254:1497-1500.

Certain embodiments of the invention are oligonucleotides with phosphorothioate backbones and oligonucleosides with heteroatom backbones, and in particular —$CH_2$—NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —O—N($CH_3$)—$CH_2$—$CH_2$— (wherein the native phosphodiester backbone is represented as —O—P—O—$CH_2$—) of the above referenced U.S. Pat. No. 5,489,677, and the amide backbones of the above referenced U.S. Pat. No. 5,602,240. Also contemplated are oligonucleotides having morpholino backbone structures of the above-referenced U.S. Pat. No. 5,034,506.

Modified Sugars

Modified oligonucleotides may also contain one or more substituted sugar moieties. Contemplated oligonucleotides comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3]_2$, where n and m are from 1 to about 10. Other preferred oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A contemplated modification includes 2'-methoxyethoxy (2'-O—$CH_2CH_2OCH_3$, also known as 2'-O-(2-methoxyethyl) or 2'-MOE) (Martin et al., *Helv. Chim. Acta,* 1995, 78, 486-504) i.e., an alkoxyalkoxy group. A further contemplated modification includes 2'-dimethylaminooxyethoxy, i.e., a $O(CH_2)_2ON(CH_3)_2$ group, also known as 2'-DMAOE, as described in examples hereinbelow, and 2'-dimethylaminoethoxyethoxy (also known in the art as 2'-O-dimethyl-amino-ethoxy-ethyl or 2'-DMAEOE), i.e., 2'-O—$CH_2$—O—$CH_2$—N($CH_3$)$_2$, also described in examples hereinbelow.

Other contemplated modifications include 2'-methoxy (2'-O—$CH_3$), 2'-aminopropoxy (2'-$OCH_2CH_2CH_2NH_2$), 2'-allyl (2'-$CH_2$—CH=$CH_2$), 2'-O-allyl (2'-O—$CH_2$—CH=$CH_2$) and 2'-fluoro (2'-F). The 2'-modification may be in the arabino (up) position or ribo (down) position. A preferred 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, each of which is herein incorporated by reference in its entirety.

A further preferred modification of the sugar includes Locked Nucleic Acids (LNAs) in which the 2'-hydroxyl group is linked to the 3' or 4' carbon atom of the sugar ring, thereby forming a bicyclic sugar moiety. The linkage is preferably a methylene (—$CH_2$—)n group bridging the 2' oxygen atom and the 4' carbon atom wherein n is 1 or 2. LNAs and preparation thereof are described in WO 98/39352 and WO 99/14226.

Natural and Modified Nucleobases

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH3) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in The Concise Encyclopedia Of Polymer Science And Engineering, pages 858-859, Kroschwitz, ed. John Wiley & Sons, 1990, those disclosed by Englisch et al., Angewandte Chemie, International Edition, 1991, 30:613, and those disclosed by Sanghvi, Chapter 15, Antisense Research and Applications, pages 289-302, Crooke and Lebleu, ed., CRC Press, 1993.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,830,653; 5,763,588; 6,005,096; and 5,681,941, each of which is herein incorporated by reference, and U.S. Pat. No. 5,750,692, also herein incorporated by reference.

Conjugates

Another modification of the oligonucleotides of the invention involves chemically linking to the oligonucleotide one or more moieties or conjugates which enhance the activity, cellular distribution or cellular uptake of the oligonucleotide. These moieties or conjugates can include conjugate groups covalently bound to functional groups such as primary or secondary hydroxyl groups. Conjugate groups of the invention include chelating moieties, intercalators, reporter molecules, polyamines, polyamides, polyethylene glycols, polyethers, groups that enhance the pharmacodynamic properties of oligomers, and groups that enhance the pharmacokinetic properties of oligomers.

Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application PCT/US92/09196 and U.S. Pat. No. 6,287,860, the entire disclosure of which are incorporated herein by reference. Conjugate moieties include but are not limited to lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxycholesterol moiety. Oligonucleotides of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130 which is incorporated herein by reference in its entirety.

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941 each of which is herein incorporated by reference.

Antisense Inhibition

The hybridization of a compound of this invention with a target nucleic acid is generally referred to as "antisense." Such hybridization can lead to inhibition of translation of the target nucleic acid and is termed "antisense inhibition" herein. Such antisense inhibition is typically based upon hydrogen bonding-based hybridization of oligonucleotide strands or segments such that at least one strand or segment is cleaved, degraded, or otherwise rendered inoperable. In this regard, it is presently preferred to target specific nucleic acid molecules and their functions for such antisense inhibition.

The functions of DNA to be interfered with can include replication and transcription. Replication and transcription, for example, can be from an endogenous cellular template, a vector, a plasmid construct or otherwise. The functions of RNA to be interfered with can include functions such as translocation of the RNA to a site of protein translation, translocation of the RNA to sites within the cell which are distant from the site of RNA synthesis, translation of protein from the RNA, splicing of the RNA to yield one or more RNA species, and catalytic activity or complex formation involving the RNA which may be engaged in or facilitated by the RNA. In the context of the present invention, "modulation" and "modulation of expression" mean either an increase (stimulation) or a decrease (inhibition) in the amount or levels of a nucleic acid molecule encoding the gene, e.g., DNA or RNA. Inhibition is often the preferred form of modulation of expression and mRNA is often a preferred target nucleic acid.

In the context of this invention, "hybridization" means the pairing of complementary strands of oligomeric compounds. In the present invention, the preferred mechanism of pairing involves hydrogen bonding, which may be Watson-Crick, Hoogsteen or reversed Hoogsteen hydrogen bonding, between complementary nucleoside or nucleotide bases (nucleobases) of the strands of oligomeric compounds. For example, adenine and thymine are complementary nucleobases which pair through the formation of hydrogen bonds. Hybridization can occur under varying circumstances.

An antisense compound is specifically hybridizable when binding of the compound to the target nucleic acid interferes with the normal function of the target nucleic acid to cause a loss of activity, and there is a sufficient degree of complementarity to avoid non-specific binding of the antisense compound to non-target nucleic acid sequences under conditions in which specific binding is desired, i.e., under physiological conditions in the case of in vivo assays or therapeutic treatment, and under conditions in which assays are performed in the case of in vitro assays.

In the present invention, the phrase "stringent hybridization conditions" or "stringent conditions" refers to conditions under which a compound of the invention will hybridize to its target sequence, but to a minimal number of other sequences. Stringent conditions are sequence-dependent and will be different in different circumstances and in the context of this invention, "stringent conditions" under which oligomeric compounds hybridize to a target sequence are determined by the nature and composition of the oligomeric compounds and the assays in which they are being investigated.

"Complementary," as used herein, refers to the capacity for precise pairing between two nucleobases of an oligomeric compound. For example, if a nucleobase at a certain position of an oligonucleotide (an oligomeric compound), is capable of hydrogen bonding with a nucleobase at a certain position of a target nucleic acid, said target nucleic acid being a DNA, RNA, or oligonucleotide molecule, then the position of hydrogen bonding between the oligonucleotide and the target nucleic acid is considered to be a complementary position. The oligonucleotide and the further DNA, RNA, or oligonucleotide molecule are complementary to each other when a sufficient number of complementary positions in each molecule are occupied by nucleobases which can hydrogen bond with each other. Thus, "specifically hybridizable" and "complementary" are terms which are used to indicate a sufficient degree of precise pairing or complementarity over a sufficient number of nucleobases such that stable and specific binding occurs between the oligonucleotide and a target nucleic acid.

It is understood in the art that the sequence of an antisense compound need not be 100% complementary to that of its target nucleic acid to be specifically hybridizable. Moreover, an oligonucleotide may hybridize over one or more segments such that intervening or adjacent segments are not involved in the hybridization event (e.g., a loop structure or hairpin structure). It is preferred that the oligonucleotide portion of the compounds of the present invention comprise at least 70% sequence complementarity to a target region within the target nucleic acid, more preferably that they comprise 85% or 90% sequence complementarity, and even more preferably comprise 95% sequence complementarity to the target region within the target nucleic acid sequence to which they are targeted. For example, a compound of the present invention in which 18 of 20 nucleobases of the compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, a compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of a compound with a region of a target nucleic acid can be determined routinely using BLAST programs (basic local alignment search tools) and Power-BLAST programs known in the art (Altschul et al., *J. Mol. Biol.*, 1990, 215:403-410; Zhang et al., *Genome Res.*, 1997, 7:649-656). For compounds of the present invention having hydroxynucleobases and/or synthetic analogs (such as other synthetic nucleobases), complementarity can be assessed by the synthetic analogs specificity for a particular nucleobase of the target nucleic acid.

While the preferred form of antisense compound is a single-stranded antisense oligonucleotide, in many species the introduction of double-stranded structures, such as double-stranded RNA (dsRNA) molecules, has been shown to induce potent and specific antisense-mediated reduction of the function of a gene or its associated gene products. This phenomenon occurs in both plants and animals and is believed to have an evolutionary connection to viral defense and transposon silencing.

The first evidence that dsRNA could lead to gene silencing in animals came in 1995 from work in the nematode, *Caenorhabditis elegans* (Guo et al., *Cell*, 1995, 81:611-620). Montgomery et al. have shown that the primary interference effects of dsRNA are posttranscriptional (Montgomery et al., *Proc. Natl. Acad. Sci. USA*, 1998, 95:15502-15507). The posttranscriptional antisense mechanism defined in *Caenorhabditis elegans* resulting from exposure to double-stranded RNA (dsRNA) has since been designated RNA interference (RNAi). This term has been generalized to mean antisense-mediated gene silencing involving the introduction of dsRNA leading to the sequence-specific reduction of endogenous targeted mRNA levels (Fire et al., Nature, 1998, 391:806-811). Recently, it has been shown that it is, in fact, the single-stranded RNA oligomers of antisense polarity of the dsRNAs which are the potent inducers of RNAi (Tijsterman et al., *Science,* 2002, 295:694-697).

Formulations

The compounds of the invention may also be admixed, encapsulated, conjugated or otherwise associated with other molecules, molecule structures or mixtures of compounds, as for example, liposomes, carriers, diluents, receptor-targeted molecules, oral, rectal, topical or other formulations, for assisting in uptake, distribution and/or absorption. Representative United States patents that teach the preparation of such uptake, distribution and/or absorption-assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

The antisense compounds of the invention encompass any pharmaceutically acceptable salts, esters, or salts of such esters, or any other compound which, upon administration to an animal, including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE ((S acetyl-2-thioethyl) phosphate) derivatives according to the methods disclosed in WO 93/24510 to Gosselin et al., published Dec. 9, 1993 or in WO 94/26764 and U.S. Pat. No. 5,770,713 to Imbach et al.

The term "pharmaceutically acceptable salts" refers to physiologically and pharmaceutically acceptable salts of the compounds of the invention: i.e., salts that retain the desired biological activity of the parent compound and do not impart undesired toxicological effects thereto. For oligonucleotides, preferred examples of pharmaceutically acceptable salts and their uses are further described in U.S. Pat. No. 6,287,860, which is incorporated herein in its entirety.

The present invention also includes pharmaceutical compositions and formulations which include the antisense compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

Pharmaceutical compositions of the present invention include, but are not limited to, solutions, emulsions, foams and liposome-containing formulations. The pharmaceutical compositions and formulations of the present invention may comprise one or more penetration enhancers, carriers, excipients, diluents, or other active or inactive ingredients.

Emulsions are typically heterogenous systems of one liquid dispersed in another in the form of droplets usually exceeding 0.1 µm in diameter. Emulsions may contain additional components in addition to the dispersed phases, and the active drug which may be present as a solution in either the aqueous phase, oily phase or itself as a separate phase. Microemulsions are included as an embodiment of the present invention. Emulsions and their uses are well known in the art and are further described in U.S. Pat. No. 6,287,860, which is incorporated herein in its entirety.

Formulations of the present invention include liposomal formulations. As used in the present invention, the term "liposome" means a vesicle composed of amphiphilic lipids arranged in a spherical bilayer or bilayers. Liposomes are unilamellar or multilamellar vesicles which have a membrane formed from a lipophilic material and an aqueous interior that contains the composition to be delivered. Cationic liposomes are positively charged liposomes which are believed to interact with negatively charged DNA molecules to form a stable complex. Liposomes that are pH sensitive or negatively charged are believed to entrap DNA rather than complex with it. Both cationic and noncationic liposomes have been used to deliver DNA to cells, and can be used to deliver compounds of the invention.

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860, which is incorporated herein in its entirety.

The pharmaceutical formulations and compositions of the present invention may also include surfactants. The use of surfactants in drug products, formulations and in emulsions is well known in the art. Surfactants and their uses are further described in U.S. Pat. No. 6,287,860, which is incorporated herein in its entirety.

In one embodiment, the present invention employs various penetration enhancers to effect the efficient delivery of nucleic acids, particularly oligonucleotides. In addition to aiding the diffusion of non-lipophilic drugs across cell membranes, penetration enhancers also enhance the permeability of lipophilic drugs. Penetration enhancers may be classified as belonging to one of five broad categories, i.e., surfactants, fatty acids, bile salts, chelating agents, and non-chelating non-surfactants. Penetration enhancers and their uses are further described in U.S. Pat. No. 6,287,860, which is incorporated herein in its entirety.

One of skill in the art will recognize that formulations are routinely designed according to their intended use, i.e. route of administration.

Preferred formulations for topical administration include those in which the compounds of the invention are in admixture with a topical delivery agent such as lipids, liposomes, fatty acids, fatty acid esters, steroids, chelating agents and surfactants. Preferred lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA).

For topical or other administration, compounds of the invention may be encapsulated within liposomes or may form complexes thereto, in particular to cationic liposomes. Alternatively, compounds may be complexed to lipids, in particular to cationic lipids. Preferred fatty acids and esters, pharmaceutically acceptable salts thereof, and their uses are further described in U.S. Pat. No. 6,287,860, which is incorporated herein in its entirety. Topical formulations are described in detail in U.S. patent application Ser. No. 09/315, 298 filed on May 20, 1999, which is incorporated herein by reference in its entirety.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Preferred oral formulations are those in which compounds of the invention are administered in conjunction with one or more penetration enhancers surfactants and chelators. Preferred surfactants include fatty acids and/or esters or salts thereof, bile acids and/or salts thereof. Preferred bile acids/salts and fatty acids and their uses are further described in U.S. Pat. No. 6,287,860, which is incorporated herein in its entirety. Also preferred are combinations of penetration enhancers, for example, fatty acids/salts in combination with bile acids/salts. A particularly preferred combination is the sodium salt of lauric acid, capric acid and UDCA. Further penetration enhancers include polyoxyethylene-9-lauryl ether, polyoxyethylene-20-cetyl ether. Compounds of the invention may be delivered orally, in granular form including sprayed dried particles, or complexed to form micro or nanoparticles. Complexing agents and their uses are further described in U.S. Pat. No. 6,287, 860, which is incorporated herein in its entirety. Oral formulations and their preparation are described in detail in U.S. application Ser. Nos. 09/108,673, 09/315,298, and 10/071, 822, each of which is incorporated herein by reference in their entirety.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Certain embodiments of the invention provide pharmaceutical compositions containing one or more compounds of the invention and one or more other chemotherapeutic agents which function by a non-antisense mechanism. Examples of such chemotherapeutic agents include but are not limited to cancer chemotherapeutic drugs such as daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. Combinations of antisense compounds and other non-antisense drugs are also within the scope of this invention. Two or more combined compounds may be used together or sequentially.

In another related embodiment, compositions of the invention may contain one or more antisense compounds, particularly oligonucleotides, targeted to a first nucleic acid and one or more additional antisense compounds targeted to a second nucleic acid target. Alternatively, compositions of the invention may contain two or more antisense compounds targeted to different regions of the same nucleic acid target. Numerous examples of antisense compounds are known in the art. Two or more combined compounds may be used together or sequentially.

Dosing

The formulation of therapeutic compositions and their subsequent administration (dosing) is believed to be within the skill of those in the art, and determined, e.g., by dos-response, toxicity, and pharmacokinetic studies. Dosing is dependent on severity and responsiveness of the disease state to be treated, with the course of treatment lasting from several days to several months, or until a cure is effected or a diminution of the disease state is achieved. Dosing may continue indefinitely for chronic disease states or conditions for which diminution but no cure can be achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. In general, dosage is from 0.01 µg to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 µg to 100 g per kg of body weight, once or more daily, to once every 20 years.

Application of Compounds of the Present Invention

The compounds of the present invention may be used in vitro or in vivo for modifying the phenotype of cells, or for limiting the proliferation of pathogens such as viruses, bacteria, protists, *Mycoplasma* species, *Chlamydia* or the like, or for inducing morbidity in neoplastic cells or specific classes of normal or diseased cells. Thus, the compounds may be administered to an organism which is subject to or in a diseased state. When administered to an organism, the compounds may be used to treat infection by a variety of pathogens, for example, enterotoxigenic bacteria, *Pneumococci, Neisseria* organisms, *Giardia* organisms, and *Entamoebas*. The compounds may also be used as cytotoxic or cytostatic agents for neoplastic cells, such as carcinoma cells, sarcoma cells, and lymphoma cells. The compounds may be used to modulate the function of immune system cells such as specific B-cells; specific T-cells, such as helper cells, suppressor cells, cytotoxic T-lymphocytes (C), and natural killer (NX) cells. Modulation of immune function using the compounds of the present invention can be useful in treatment of a variety of diseases such as cancer and immune system disease.

The compounds may be selected so as to be capable of interfering with transcription or expression of proteins by any of the mechanisms involved with the binding of the oligonucleotide of the compound to its target sequence. These mechanisms may include interference with processing, inhibition of transport across the nuclear membrane, cleavage by endonucleases, or the like.

The oligonucleotide of the compound may be complementary to nucleic acid sequences such as those encoding growth factors, lymphokines, immunoglobulins, T-cell receptor sites, MHC antigens, DNA or RNA polymerases, antibiotic resistance, multiple drug resistance (mdr), genes involved with metabolic processes, such as the formation of amino acids, nucleic acids, or the like. The oligonucleotide may be complementary to nucleic acid sequences including introns or flanking sequences associated with the open reading fines.

The compounds of the present invention may be used in the treatment of infectious diseases, cancers, autoimmune diseases and conditions associated with organ transplants. In the treatment of infectious diseases, the target nucleic acid sequences include those genes associated with AIDS, CMV, herpes, drug resistance plasmids, and trypanosomes. In the treatment of cancer, the target nucleic acid sequences can be DNA or RNA associated with oncogenes, tumor suppressor genes, and related genes. Additionally, the compounds of the present invention may also target genes associated with drug resistance and their gene products. For the treatment of autoimmune diseases, the compounds can, for example, target nucleic acid sequences associated with rheumatoid arthritis, Type I diabetes, systemic lupus and multiple sclerosis.

As disclosed herein, the present invention is not limited to any type of target gene or nucleotide sequence and is applicable to any gene for any organism or virus, for example. But the following classes of possible target genes are listed for illustrative purposes: developmental genes (e.g., adhesion molecules, cyclin kinase inhibitors, Wnt family members, Pax family members, Winged helix family members, Hox family members, cytokines/lymphokines and their receptors, growth/differentiation factors and their receptors, neurotransmitters and their receptors); oncogenes (e.g., ABL1—GenBank Accession No. BC 107069; BCL1—GenBank Accession No. NM 053056; BCL2—GenBank Accession No. NM 181505; BCL6—GenBank Accession No. NM 138931; CBFA2—GenBank Accession No. NM 001001890; CBL—GenBank Accession No. NM 138392; CSF1R—GenBank Accession No. CH471062; ERBA—GenBank Accession No. NM 021724; ERBB—GenBank Accession No. NM 138573; ERBB2—GenBank Accession No. NM 181505; ETS1—GenBank Accession No. NM 005238; ETV6—GenBank Accession No. NM 002336; FGR—GenBank Accession No. NM 153048; FLT—GenBank Accession No. NM 004119; FOS—GenBank Accession No. NM 001080547; FYN—GenBank Accession No. NM 016363; HCR—GenBank Accession No. NM 003965; HRAS—GenBank Accession No. NM 007069; SOCS6—GenBank Accession No.—NM 004232; KRAS—GenBank Accession No. NM 176795; LCK—GenBank Accession No.; LYN—GenBank Accession No. NM 001042771; MET—GenBank Accession No. NM 017956; MDM2—GenBank Accession No. NM 022045; MLL—GenBank Accession No. NM 012081; MYB—GenBank Accession No. NM 014520; MYC—GenBank Accession No. NM 032789; MYCL1—GenBank Accession No. NM 001033082; MYCN—GenBank Accession No. NM 005378; NRAS—GenBank Accession No. NM 002524; PIM1—GenBank Accession No.; PML—GenBank Accession No. NM 002648; RET—GenBank Accession No. NM 020630; SRC—GenBank Accession No. NM 016848; TAL1—GenBank Accession No.; NM 003189; TCL1—GenBank Accession No. NM 021966; TLX1—GenBank Accession No. NM 005521; and YES—GenBank Accession No. NM 006106); tumor suppressor genes (e.g., APC—GenBank Accession No. NM 000038; BRCA1—GenBank Accession No. NG 005905; BRCA2—GenBank Accession No. NM 007305; MADH4—GenBank Accession No. NM 005359; MCC—GenBank Accession No. NM 022132; NF1—GenBank Accession No. NM 017940; NF2—GenBank Accession No. NM 181831; RB1—GenBank Accession No. NM 000321; TP53—GenBank Accession No. EF432550; and WT1—GenBank Accession No. NM 024426); enzymes (e.g., ACC synthases and oxidases, ACP desaturases and hydroxylases, ADP-glucose pyrophorylases, ATPases, alcohol dehydrogenases, amylases, amyloglucosidases, catalases, cellulases, chalcone synthases, chitinases, cyclooxygenases, decarboxylases, dextrinases, DNA and RNA polymerases, galactosidases, glucanases, glucose oxidases, granule-bound starch synthases, GTPases, helicases, hemicellulases, integrases, inulinases, invertases, isomerases, kinases, lactases, lipases, lipoxygenases, lysozymes, nopaline synthases, octopine synthases, pectinesterases, peroxidases, phosphatases, phospholipases, phosphorylases, phytases, plant growth regulator synthases, polygalacturonases, proteinases and peptidases, pullanases, recombinases, reverse transcriptases, RUBISCOs, topoisomerases, and xylanases); genes of pathogenic microbes (e.g., *Pseudomonas* species, *Escherichia coli, Plasmodium*, and *Chlamydia*); genes of pathogenic viruses (e.g., HIV, hepatitis, herpes, influenza, rhinoviruses, adenoviruses, and negative strand RNA viruses); commercially relevant genes (e.g., genes for antibodies, growth factor genes, and hormone genes); animal viruses (e.g., FMDV—GenBank Accession No. DQ902653 and FLV—GenBank Accession No. DQ531584); plant viruses (e.g., PVY—GenBank Accession No. EF470241; TMV—GenBank Accession No. AB264547; and CMV—GenBank Accession No. NC 002034).

In addition to binding nucleic acids, the compounds of the present invention may also be employed for binding to proteins including, but not limited to, ligands, receptors, and/or enzymes, whereby the compounds inhibit the activity of the proteins.

"Targeting" an antisense compound to a particular nucleic acid molecule, in the context of this invention, can be a multistep process. The process usually begins with the identification of a target nucleic acid whose function is to be modulated. This target nucleic acid may be, for example, a cellular gene (or mRNA transcribed from the gene) whose expression is associated with a particular disorder or disease state, or a nucleic acid molecule from an infectious agent.

The targeting process usually also includes determination of at least one target region, segment, or site within the target nucleic acid for the antisense interaction to occur such that the desired effect, e.g., modulation of expression, will result. Within the context of the present invention, the term "region" is defined as a portion of the target nucleic acid having at least one identifiable structure, function, or characteristic. Within regions of target nucleic acids are segments. "Segments" are defined as smaller or sub-portions of regions within a target nucleic acid. "Sites," as used in the present invention, are defined as positions within a target nucleic acid.

Since, as is known in the art, the translation initiation codon is typically 5' AUG (in transcribed mRNA molecules; 5' ATG in the corresponding DNA molecule), the translation initiation codon is also referred to as the "AUG codon," the "start codon" or the "AUG start codon". A minority of genes have a translation initiation codon having the RNA sequence 5' GUG, 5' UUG or 5' CUG, and 5' AUA, 5' ACG and 5' CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA transcribed from a gene encoding Interleukin 18, regardless of the sequence(s) of such codons. It is also known in the art that a translation termination codon (or "stop codon") of a gene may have one of three sequences, i.e., 5' UAA, 5' UAG and 5' UGA (the corresponding DNA sequences are 5' TAA, 5' TAG and 5' TGA, respectively).

The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. Consequently, the "start codon region" (or "translation initiation codon region") and the "stop codon region" (or "translation termination codon region") are all regions which may be targeted effectively with the antisense compounds of the present invention.

The open reading frame (ORF) or "coding region," which is known in the art to refer to the region between the translation initiation codon and the translation termination codon, is also a region which may be targeted effectively. Within the context of the present invention, a preferred region is the intragenic region encompassing the translation initiation or termination codon of the open reading frame (ORF) of a gene.

Other target regions include the 5' untranslated region (5'UTR), known in the art to refer to the portion of an mRNA in the 5' direction from the translation initiation codon, and thus including nucleotides between the 5' cap site and the translation initiation codon of an mRNA (or corresponding nucleotides on the gene), and the 3' untranslated region (3'UTR), known in the art to refer to the portion of an mRNA in the 3' direction from the translation termination codon, and thus including nucleotides between the translation termination codon and 3' end of an mRNA (or corresponding nucleotides on the gene). The 5' cap site of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap site. It is also preferred to target the 5' cap region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. Targeting splice sites, i.e., intron-exon junctions or exon-intron junctions, may also be particularly useful in situations where aberrant splicing is implicated in disease, or where an overproduction of a particular splice product is implicated in disease. Aberrant fusion junctions due to rearrangements or deletions are also preferred target sites. mRNA transcripts produced via the process of splicing of two (or more) mRNAs from different gene sources are known as "fusion transcripts." It is also known that introns can be effectively targeted using antisense compounds targeted to, for example, DNA or pre-mRNA.

It is also known in the art that alternative RNA transcripts can be produced from the same genomic region of DNA. These alternative transcripts are generally known as "variants". More specifically, "pre-mRNA variants" are transcripts produced from the same genomic DNA that differ from other transcripts produced from the same genomic DNA in either their start or stop position and contain both intronic and exonic sequence.

Upon excision of one or more exon or intron regions, or portions thereof during splicing, pre-mRNA variants produce smaller "mRNA variants". Consequently, mRNA variants are processed pre-mRNA variants and each unique pre-mRNA variant must always produce a unique mRNA variant as a result of splicing. These mRNA variants are also known as "alternative splice variants". If no splicing of the pre-mRNA variant occurs then the pre-mRNA variant is identical to the mRNA variant.

It is also known in the art that variants can be produced through the use of alternative signals to start or stop transcription and that pre-mRNAs and mRNAs can possess more that one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites. Within the context of the invention, the types of variants described herein are also preferred target nucleic acids.

The locations on the target nucleic acid to which the preferred antisense compounds hybridize are herein below referred to as "preferred target segments." As used herein the term "preferred target segment" is defined as at least a 5-nucleobase portion of a target region to which an active antisense compound is targeted. While not wishing to be bound by theory, it is presently believed that these target segments represent portions of the target nucleic acid which are accessible for hybridization.

While the specific sequences of certain preferred target segments are set forth herein, one of skill in the art will recognize that these serve to illustrate and describe particular embodiments within the scope of the present invention. Additional preferred target segments may be identified by one having ordinary skill.

Target segments 5-150 nucleobases in length comprising a stretch of at least five consecutive nucleobases selected from within the illustrative preferred target segments are considered to be suitable for targeting as well.

Target segments can include DNA or RNA sequences that comprise at least the 5 consecutive nucleobases from the 5'-terminus of one of the illustrative preferred target segments (the remaining nucleobases being a consecutive stretch of the same DNA or RNA beginning immediately upstream of the 5'-terminus of the target segment and continuing until the DNA or RNA contains about 5 to about 150 nucleobases). Similarly preferred target segments are represented by DNA or RNA sequences that comprise at least the 5 consecutive nucleobases from the 3'-terminus of one of the illustrative preferred target segments (the remaining nucleobases being a consecutive stretch of the same DNA or RNA beginning immediately downstream of the 3'-terminus of the target segment and continuing until the DNA or RNA contains about 5 to about 150 nucleobases). One having skill in the art armed with the preferred target segments illustrated herein will be able, without undue experimentation, to identify further preferred target segments.

Once one or more target regions, segments or sites have been identified, antisense compounds are synthesized which are sufficiently complementary to the target, i.e., hybridize sufficiently well and with sufficient specificity, to give the desired effect, and incorporate at least one hydroxynucleobase which is complementary to a nucleobase in the sequence of the target region, segment, or site, and further incorporates a chelating moiety as described herein. The antisense compound is then contacted with a ion of a metal to allow for complexation of the ion to the compound. This resulting compound can then be used in antisense therapy mechanisms.

Kits and Diagnostic Tools

The compounds of the present invention can be utilized for diagnostics, therapeutics, prophylaxis and as research reagents and kits. Furthermore, antisense oligonucleotides, which are able to inhibit gene expression with exquisite specificity, are often used by those of ordinary skill to elucidate the function of particular genes or to distinguish between functions of various members of a biological pathway.

For use in kits and diagnostics, the compounds of the present invention, either alone or in combination with other compounds or therapeutics, can be used as tools in differential and/or combinatorial analyses to elucidate expression patterns of a portion or the entire complement of genes expressed within cells and tissues.

As one nonlimiting example, expression patterns within cells or tissues treated with one or more antisense compounds are compared to control cells or tissues not treated with antisense compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds which affect expression patterns.

Examples of methods of gene expression analysis known in the art include DNA arrays or microarrays (Brazma and Vilo, *FEBS Lett.*, 2000, 480:17-24; Celis, et al., *FEBS Lett.*, 2000, 480:2-16), SAGE (serial analysis of gene expression) (Madden, et al., *Drug Discov. Today*, 2000, 5:415-425), READS (restriction enzyme amplification of digested cDNAs) (Prashar and Weissman, *Methods Enzymol.*, 1999, 303:258-72), TOGA (total gene expression analysis) (Sutcliffe, et al., *Proc. Natl. Acad. Sci. U.S.A.*, 2000, 97:1976-81), protein arrays and proteomics (Celis, et al., *FEBS Lett.*, 2000, 480:2-16; Jungblut, et al., *Electrophoresis*, 1999, 20:2100-10), expressed sequence tag (EST) sequencing (Celis, et al., *FEBS Lett.*, 2000, 480:2-16; Larsson, et al., *J. Biotechnol.*, 2000, 80:143-57), subtractive RNA fingerprinting (SuRF) (Fuchs, et al., *Anal. Biochem.*, 2000, 286:91-98; Larson, et al., *Cytometry*, 2000, 41:203-208), subtractive cloning, differential display (DD) (Jurecic and Belmont, *Curr. Opin. Microbiol.*, 2000, 3:316-21), comparative genomic hybridization (Carulli, et al., *J. Cell Biochem. Suppl.*, 1998, 31:286-96), FISH (fluorescent in situ hybridization) techniques (Going and Gusterson, *Eur. J. Cancer*, 1999, 35:1895-904) and mass spectrometry methods (To, *Comb. Chem. High Throughput Screen*, 2000, 3:235-41).

The specificity and sensitivity of antisense is also harnessed by those of skill in the art for therapeutic uses. Antisense compounds have been employed as therapeutic moieties in the treatment of disease states in animals, including humans. Antisense oligonucleotide drugs, including ribozymes, have been safely and effectively administered to humans and numerous clinical trials are presently underway. It is thus established that antisense compounds can be useful therapeutic modalities that can be configured to be useful in treatment regimes for the treatment of cells, tissues and animals, especially humans.

For therapeutics, a subject, preferably a human, suspected of having a disease or disorder which can be treated by modulating the expression of a target nucleic acid is treated by administering antisense compounds in accordance with this invention. For example, in one non-limiting embodiment, the methods comprise the step of administering to the subject in need of treatment, a therapeutically effective amount of an antisense compound. The compounds of the invention can be utilized in pharmaceutical compositions by adding an effective amount of a compound to a suitable pharmaceutically acceptable diluent or carrier. Use of the compounds and methods of the invention may also be useful prophylactically.

Additional aspects and details of the disclosure will be apparent from the following examples, which are intended to be illustrative rather than limiting.

EXAMPLES

Synthesis of Oligonucleotides with Modified Nucleotides

Synthesis of GCAGCCAAAACGTCCN (SEQ ID NO: 1) or CCTTCGN(N=5-OH dC) (SEQ ID NO: 5)

5-Hydroxy-2'-deoxycytidine 5'-triphosphate was synthesized using a procedure similar to that described for the synthesis of 5-hydroxycytidine 5'-diphosphate. Twenty five mg (45 µmole) of dCTP (as the sodium salt) was dissolved in 200 µl of water and then cooled to 4° C. Bromine was slowly added with vigorous mixing to the dCTP solution until the yellow color persisted. To remove excess bromine, 7 µl of cyclohexene was added with shaking, followed by 0.1 ml of 2,4,6-collidine. The emulsion was incubated for about 2 hours at 37° C. and then extracted with ether (4×0.5 ml). The aqueous layer was evaporated under vacuum, redissolved in water, and loaded on a DEAE-Sephadex A-25 column (about 80 ml, $HCO_3^-$ form). The fraction containing triphosphates was eluted from the column with a linear gradient of triethylammonium bicarbonate (TEAB), pH 7.5-8 (5 mM to 0.8 M). Fractions containing a mixture of nucleoside triphosphates were pooled and evaporated several times with 50% ethanol to remove TEAB. 5-OHdCTP was further purified twice on a Mono Q column using first a linear gradient of NaCl from 5 mM to 0.7 M in 20 mM Tris-HCl buffer, pH 7.5, and finally a linear gradient from 5 mM to 0.7 M sodium phosphate buffer, pH 3.5. The peak of 5-OHdCTP was collected, diluted with water, and reloaded on a DEAE sephadex A-25 column (2.5 ml, $HCO_3^-$ form). The column washed with 0.1 M ammonium bicarbonate to remove salt followed by the elution of 5-OHdCTP with 0.6 M ammonium bicarbonate. The ammonium bicarbonate was removed by repeated evaporation with 50% ethanol. The yield of 5-OHdCTP was about 25-30%.

The molar absorptivity [ε=7700 (X,=292 nm)] (15) was used to calculate the amount of 5-OHdCTP.

Oligonucleotides containing a single, internal 5-OHdC were prepared by a modification of the method previously described. One to 2.5 nmoles of GCAGCCAAAACGTCC (SEQ ID NO: 2) or CCTTCG (SEQ ID NO: 3) were incubated for 30 min. at 30° C. in 65 μl of buffer containing 100 mM sodium cacodylate pH 7.0, 1 mM CoCl2, 0.1 mM EDTA, 50 μg/ml of BSA, 0.1 mM DTT, 10 μM 5-OHdCTP, and 100 units of terminal deoxynucleotidyl transferase. The oligonucleotides, extended from the 3'-end with a single 5-OHdCMP, were then HPLC purified on a Partisphere SAX column (0.4×12.5 cm, Whatman) using a linear gradient of sodium phosphate buffer, pH 6.3 (from 5 mM to 0.5 M over 60 min), containing 25% acetonitrile. The purified extended oligonucleotides, GCAGCCAAAACGTCCN (SEQ ID NO: 4) or CCTTCGN (SEQ ID NO: 5) (N=5-OHdC or 5-OHdU), were desalted using a NEP-5 column (Pharmacia).

Synthesis of Rare Earth Metal Complexes and their Conjugates with Oligonucleotides Materials Cyclam (Aldrich, 98%), 4-chloromethylbenzoic acid (Aldrich, 95%), trifluoroethylacetate (Aldrich, 99%), N-hydroxysuccinimide (Aldrich, 97%), 1-(3-dimethylamino)-3-ethylcarbodiimide hydrochloride (Sigma, Prot. Seq. Grade), Europium triflate (Aldrich, 98%), Lanthanum triflate (Aldrich, 99.999%), Silicagel (Acros Organics, USA) having particle size of 60-200 μm and pore size of 4 nm, Sephadex G-25 (Sigma-Aldrich) with a particle size of 40-125 μm and capacity of 3-4 meq/g.

Synthesis of 4-(1,4,8,11-tetraazacyclotetradec-1-ylmethyl)-benzoic acid

To solution of Cyclam (0.913 g, 4.5 mmol) dissolved in a mixture of ethanol:water (5:1 by vol.) (18 ml) was added a solution of 4-chloromethylbenzoic acid (0.157 g, 0.92 mmol) in aqueous LiOH (53 mg in 4 ml of water). This mixture was thereafter refluxed vigorously with stirring for 5 hours. Then the solvent was removed at reduced pressure, and the residue was dissolved in 13 ml of water. The aqueous solution obtained was then extracted with chloroform (10 times 3 ml) and the aqueous layer was concentrated at reduced pressure down to 2 ml. The product as a white solid was precipitated by adding the solution of concentrated HCl and ethanol and purified by recrystallizing from ethanol/water/HCl to yield 0.205 g of the title compound. According to the LC-MS, the assay of 4-(1,4,8,11-tetraazacyclotetradec-1-ylmethyl)-benzoic acid hydrochloride was >95%.

Synthesis of 4-(4,8,11-Tris-(2,2,2-trifluoroacetyl)-1,4,8,11-tetraazacyclotetradec-1-ylmethyl)-benzoic acid To a two-neck round bottom flask purged with argon was added successively 4-(1,4,8,11-tetraazacyclotetradec-1-ylmethyl)-benzoic acid (90 mg, 0.24 mmol), dry methanol (1 ml), dry triethyl amine (0.5 ml) and trifluoroethylacetate (1.7 ml). All following procedures were carried on in argon atmosphere. The mixture was stirred for 60 hours. After that the solvents were removed at reduced pressure and the residue was taken up in dry tetrahydrofurane (5 ml). The THF solution was filtered and the solvent removed at reduced pressure. The residue was dried in vacuo for 4 hours to produce 0.54 g of oily compound. MS m/z 623.5 M[$C_{24}H_{27}F_9N_4O_5$]+1.

Synthesis of 4-(4,8,11-Tris-(2,2,2-trifluoroacetyl)-1,4,8,11-tetraazacyclotetradec-1-ylmethyl)-benzoic acid 2,5-dioxopyrrolidin-1-yl ester The flask containing 4-(4,8,11-Tris-(2,2,2-trifluoroacetyl)-1,4,8,11-tetraazacyclo-tetradec-1-ylmethyl)-benzoic acid (0.54 g) was purged with argon and successively were added dry THF (1.2 ml), N-hydroxysuccinimide (28 mg, 0.24 mmol) and 1-(3-dimethylamino)-3-ethylcarbodiimide hydrochloride (51.6 mg, 0.27 mmol). This mixture was stirred under argon for 60 hours at room temperature. Then the solvent was removed at reduced pressure, the residue was dissolved in a minimum amount of chloroform and passed through a silica gel column. The product was eluted with chloroform:methanol (50:1). After concentrating with rotary evaporator and drying in vacuo, 4-(4,8,11-Tris-(2,2,2-trifluoroacetyl)-1,4,8,11-tetraazacyclotetradec-1-ylmethyl)-benzoic acid 2,5-dioxopyrrolidin-1-yl ester was collected as a white solid substance with the yield of 70 mg. LC-MS spectra of the product confirmed that the main fraction has a mass of 721 [M($C_{28}H_{30}F_9N_5O_7$)+1], which gives a fragment with a mass of 623 [(M-$C_2F_3O$)+1].

The minor fraction (~1%) was detected as:

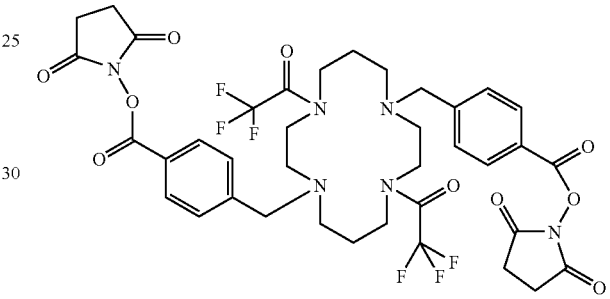

MS m/z 855.7 [M($C_{38}H_{40}F_6N_6O_{10}$)+1]

General procedure for making the La and Eu complexes of 4-(4,8,11-Tris-(2,2,2-trifluoroacetyl)-1,4,8,11-tetraazacyclotetradec-1-ylmethyl)-benzoic acid 2,5-dioxopyrrolidin-1-yl ester The equimolar (~20 μmol) mixture of 4-(4,8,11-Tris-(2,2,2-trifluoroacetyl)-1,4,8,11-tetraazacyclotetradec-1-ylmethyl)-benzoic acid 2,5-dioxopyrrolidin-1-yl ester and lanthanide triflate, La($CF_3SO_3$)$_3$ or Eu($CF_3SO_3$)$_3$, in dry ethanol (2 ml) was stirred in argon atmosphere at room temperature for 22 hours. After that, the solvents were removed at reduced pressure, and the residue was taken up by acetonitrile (0.5 ml). After addition of ether (0.7 ml), the mixture was kept at freezer for 48 hours, filtered and then taken to dryness under vacuo to yield the pale yellow solids of La and Eu complexes of 4-(4,8,11-Tris-(2,2,2-trifluoroacetyl)-1,4,8,11-tetraazacyclotetradec-1-ylmethyl)-benzoic acid 2,5-dioxopyrrolidin-1-yl ester.

The synthesis of the other ligands may be made using known synthetic techniques. See, e.g., U.S. Pat. Nos. 6,984,734; 6,127,121; and 5,684,149, each of which is incorporated in its entirety by reference herein.

Conjugation of La and Eu complexes of 4-(4,8,11-Tris-(2,2,2-trifluoroacetyl)-1,4,8,11-tetraazacyclotetradec-1-ylmethyl)-benzoic acid 2,5-dioxopyrrolidin-1-yl ester to oligonucleotide Two differently modified 20-mer oligonucleotides are synthesized: 5'-CTT CTG GCC GTT TAC GTC GN-3' (N=5-OH—C or C) (SEQ ID NO: 6).

About 10 nmol of each oligonucleotide is dissolved in 300 μL of a 200 mM NaHCO$_3$ solution. The resulting solution is then added to a solution of the lanthanide complex of the tetraaza macrocycle (0.64 mg) in dioxane (200 μL). The resultant mixture is stirred vigorously for 3 h at room temperature. Then, the mixture is passed through the Sephadex G-25 column (1.5×5.5 cm) packed in potassium phosphate buffer (pH 6.86). The product is eluted with the same phosphate buffer and the last 13 ml of the total 15 ml of extract are collected and reduced to the volume of ~0.5 ml in vacuo at room temperature.

In Vitro Activity Measurements

The activity of the lanthanum- and europium-complexed compounds are measured by mixing a solution of a target nucleic acid (e.g., 5'-GCG ACG TAA ACG GCC AGA AG-3' (SEQ ID NO: 7)) with each of the complexed compounds under conditions which simulate human physiological conditions (e.g., temperature and salt conditions). The compound and target nucleic acid are mixed and allowed to interact. Aliquots of the mixtures are taken out and analyzed for the presence or degradation of the target nucleic acid. Amounts of target nucleic acids are measured. The rate of degradation of the target nucleic acid directly correlates to the nuclease activity of the lanthanum- and europium-complexed compounds.

Stability of Oligonucleotides Having Hydroxy-Nucleic Acids Incorporated: 5'-CTT CTN NCC NTT TAC NTC NC-3' (N=G or 8-OH G) (SEQ ID NO: 8)

A series of oligonucleotides were labeled at the 5'-end of the polynucleotide chain with $^{35}$S-αATP with T4 polynucleotide kinase. The labeled oligonucleotides were purified and liberated from the free labeled $^{35}$S-αATP using Pharmacia PD10 gel filtration columns. The specific activity of the oligonucleotides was between 0.05-0.2 μCi/μg of oligonucleotide.

Labeled oligonucleotides (1-10 nM) were incubated in the 5 mM HEPES buffer, pH. 7.5, containing 100 nM KCl and 80% fetal bovine serum, and incubated for indicated time at the temperature of 37° C. At indicated time intervals aliquots of the of the reaction mixture were removed and diluted 5-fold with the loading dye containing 0.05% bromophenol blue, 0.05% xylene cyanol, 7M urea and 0.5×TBE buffer. The degraded oligonucleotides were analyzed using 20% polyacrylamide gel electrophoresis. The bands were cut out from the gel and the radioactivity was counted using Wallac Micro Beta scintillation counter.

Protocols used were as described in Maniatis, T., Fritsch, E. F. and Sambrook, J. Molecular Cloning: A Laboratory Manual. Cold Spring Harbor Laboratory, Cold Spring Harbor, N.Y. 1082.

The results demonstrate a distinct stabilization by the incorporation of hydroxynucleobases into the oligonucleotides (FIG. 1). The notations in FIG. 1 correspond to native oligomer (SEQ ID NO: 8 wherein all N are G) and the oligomers with one (1-mod; 5'-CTT CTN GCC GTT TAC GTC GC-3'; SEQ ID NO: 9; N=8-OH G), two (2-mod; 5'-CTT CTN GCC NTT TAC GTC GC-3'; SEQ ID NO: 10; N=8-OH G) and three (3-mod; 5'-CTT CTN GCC NTT TAC GTC NC-3'; SEQ ID NO: 11; N=8-OH G).

The presence of strongly bound tautomers appreciably increases the melting temperature of the respective nucleic acid duplexes. The measured melting temperature of a normal duplex of SEQ ID NO: 8, wherein all N are G is 67±2° C. In contrast, the melting temperature of the same oligomer with two 8-hydroxyguanine substitutions (SEQ ID NO: 10) is 71±2° C.

RNA Degradation Using Oligonucleotides Incorporating 8-Hydroxy Guanine

Figure 2:
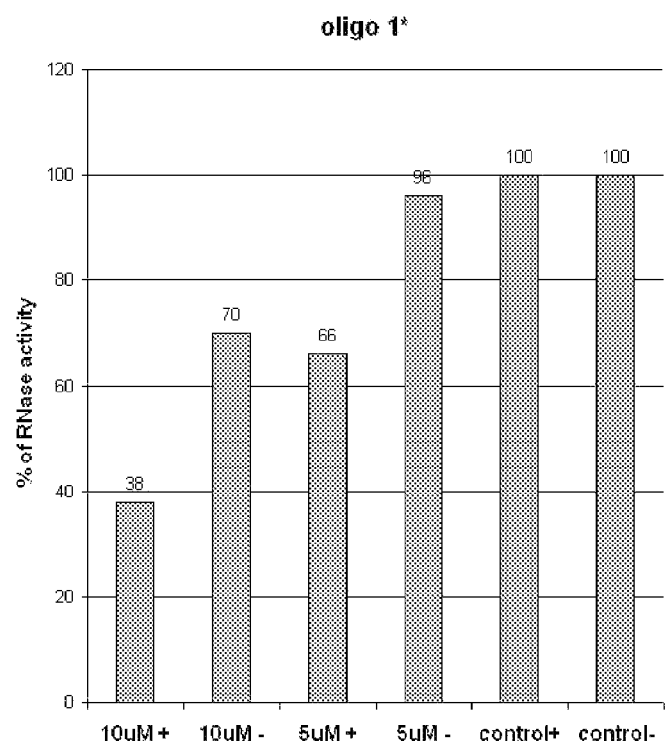
FIG. 2 is a graph depicting the amount of RNA remaining after incubation with a variety of complementary oligonucleotides.

Both $^{35}$S-labeled and unlabelled sense and antisense RNAs encoding the enhanced green fluorescent protein (eGFP) were prepared for in vitro monitoring of RNA degradation. The eGFP was cloned into pCR3.1 expression vector under the control of T7 RNA polymerase promoter in two orientations: sense and antisense orientation. Sense and antisense cGPF RNAs were synthesized in vitro using T7 RNA polymerase $^{35}$S-labeled ribonucleotide triphosphates using standard protocols. For this analysis, equal amounts of $^{35}$S-labeled RNA were incubated with different concentrations of the complementary oligonucleotides to eGFP. The oligonucleotides had either zero (SEQ ID NO: 8) or one 8-hydroxy guanine incorporated (SEQ ID NO: 9). Both the natural and the modified oligonucleotides were complexed with a lanthanide known to have ribonuclease activity. The RNA and the oligonucleotides were incubated for 1 hour at 37° C. The RNA then was analyzed on the 1% agarose gel electrophoresis. The gel was visualized with autoradiography, and the RNA bands were cut out, hydrolyzed, and counted using a Wallac scintillation counter. The quantitative results are shown in FIG. 2, which depicts the amount of undegraded RNA still remaining. Columns 1 and 3 of FIG. 2 show results from the incubation of eGFP RNA with oligonucleotide-lanthanide complexes having a 8-hydroxyguanine incorporated at 10 μM and 5 μM, respectively. Columns 2 and 4 of FIG. 2 show results from the incubation of eGFP RNA with oligonucleotide-lanthanide complexes with natural guanine at 10 μM and 5 μM, respectively. Columns 5 and 6 of FIG. 2 represent control experiments having no oligonucleotide-lanthanide complex added. The results of these experiments clearly show that oligonucleotides with one modification form a more stable complex with target eGFP RNA and enhances its degradation (compare columns 1 and 2 and column 3 and 4). The oligonucleotide-lanthanide complex containing a single 8-hydroxygunaine modification in the exhibited nuclease activity at 5 μM, while the oligonucleotide-lanthanide complex containing natural guanine exhibited virtually no nuclease activity.

Analyses of RNA degradation by lanthanide-oligonucleotide complexes. eGFP RNA was incubated with normal or modified 20 nucleotides long oligonucleotides complementary to eGFP. The incubation was at 37° C. for 1 hour. In this experiment, unlabeled RNA was used, and the results were analyzed by electrophoresis using a 1% agarose gel. The RNA on the gel was visualized by ethidium bromide staining.

Figure 3:
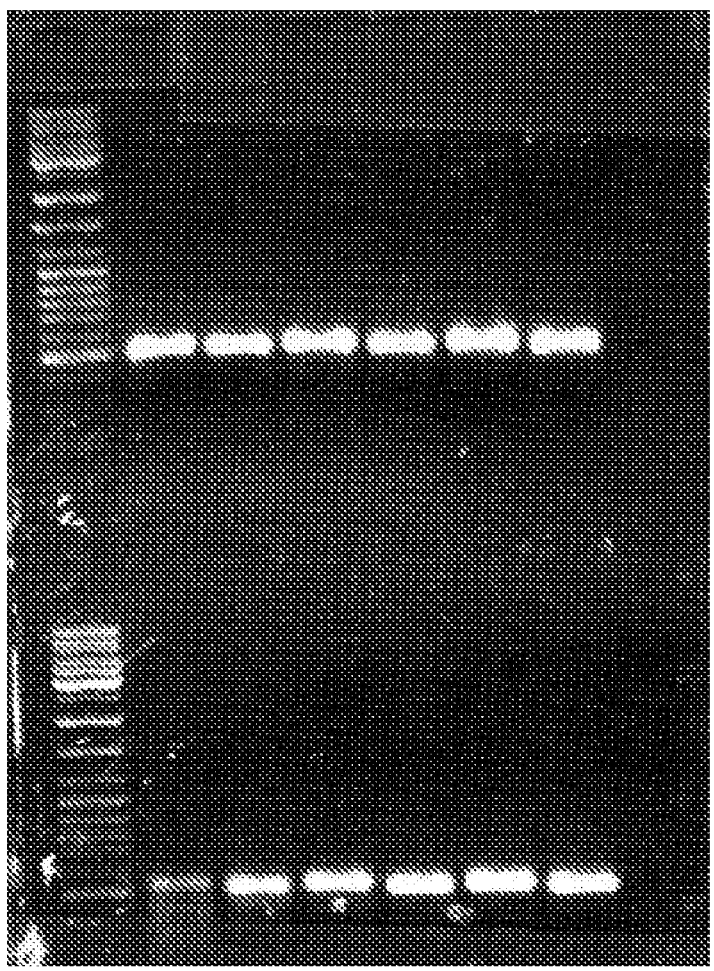
FIG. 3 is a photograph of analytical gels showing degradation of eGFP in the presence of lanthanide-oligonucleotide complexes as disclosed herein. The upper gel shows the results of incubation of unmodified oligonucleotides complexed to lanthanides with mRNA and the lower gel shows the results of the incubation of mRNA with modified oligonucleotides complexed to lanthanides. Lane 1 is the molecular weight size markers; lanes 2 and 3 show degradation in the presence of 10 μM oligonucleotide-lanthanide complexes; lanes 3 and 4 show degradation in the presence of 5 μM oligonucleotide-lanthanide complexes; lane 6 is a control experiment of the sense RNA; and lane 7 is a control experiment of the antisense RNA.

FIG. 3 shows the results of this experiment. The upper gel shows the degradation of eGFP RNA after incubation with unmodified oligonucleotide-lanthanide complex (1,4,8,11-tetraazacyclotetradecyl europium complex with SEQ ID NO: 8) and the lower gel is a modified oligonucleotide-lanthanide complex (1,4,8,11-tetraazacyclotetradecyl europium complex with SEQ ID NO: 9), where the oligonucleotide has a single modification to a hydroxynucleobase. The lanes on both the upper and lower gels are as follows: 1. Molecular weight and nucleic acid size markers; 2. Oligonucleotide-lanthanide complex at 10 μM; 3. Oligonucleotide-lanthanide complex at 10 μM; 4. Oligonucleotide-lanthanide complex at 5 μM; 5. Oligonucleotide-lanthanide complex at 5 μM; 6. Control (sense RNA); 7. Control (antisense RNA).

The results as shown in FIG. 3 indicate that an oligonucleotide with a modification is more stable and active in the complex with lanthanide.

DOCUMENTS CITED

All of the documents listed here are incorporated by reference for the materials, methods, and procedures that they teach.

U.S. Patent Documents

Cook, et al. "Substituted purines and oligonucleotide cross-linking" U.S. Pat. No. 6,232,463, May 15, 2001.
Froehler, et al. "Enhanced triple-helix and double-helix formation directed by oligonucleotides containing modified pyrimidines" U.S. Pat. No. 6,235,887; May 22, 2001.
Iyer, "Reagents and process for synthesis of oligonucleotides containing phosphorodithioate internucleoside linkages" U.S. Pat. No. 6,117,992; Sep. 12, 2000.
Meyer, Jr., et al. "Oligonucleotides containing pyrazolo[3,4-D]pyrimidines for hybridization and mismatch discrimination" U.S. Pat. No. 6,127,121; Oct. 3, 2000.
Morrow, "Metal complexes for promoting catalytic cleavage of RNA by transesterification" U.S. Pat. No. 5,684,149; Nov. 4, 1997
Short, "Modified nucleotides and methods useful for nucleic acid sequencing" U.S. Pat. No. 6,579,704, Jun. 17, 2003.
Switzer, "Antisense oligonucleotide containing compositions and method of forming duplexes" U.S. Pat. No. 6,031,086, Feb. 29, 2000.
Haner et al, "Functional terpyridine-metal complexes, a process for the preparation thereof and oligonucleotide conjugates with terpyridine-metal complexes" U.S. Pat. No. 5,925,744, Jul. 20, 1999.
Switzer, "Antisense oligonucleotides comprising 5-aminoalkyl pyrimidine nucleotides" U.S. Pat. No. 5,596,091, Jan. 21, 1997.
Wang, et al., "Sugar modified nucleosides and oligonucleotides" U.S. Pat. No. 5,681,940; Oct. 28, 1997.

Other Publications

Baker B. F., et al., Oligonucleotide-europium complex conjugate designed to cleave the 5' cap structure of the ICAM-1 transcript potentiates antisense activity in cells, *Nucl. Acid Res.*, 1999, 27:1547-1551.
Bing Zhua, et al., Binuclear lanthanide complexes as catalysts for the hydrolysis of double-stranded DNA, *Inorg. Chem. Communs.*, 1999, 2: 351-353.
Canaple, L. et al., Artificial Ribonucleases: Efficient and Specific in Vitro Cleavage of Human c-raf-1 RNA, *Bioconjugate Chem.* 2002, 13:945-951.
Crooke S T. Progress in antisense therapeutics. *Med. Res. Rev.* 1996; 16: 319-344.
Crooke, S. T. and Lebleu, B. "Antisense Research and Applications", CRC Press (1993).
Hegg E. L; Burstyn, J. L; Toward the development of metal-based synthetic nucleases and peptidases: a rationale and progress report in applying the principles of coordination chemistry, *Coord. Chem. Revs.* 1998, 173: 133-165.
Hall, J.; Hüsken D.; Pieles, U., Moser, H. E.; Häner, R, Efficient sequence-specific cleavage of RNA using novel europium complexes conjugated to oligonucleotides", *Chemistry & Biology*, 1994, 1: 185-190.
Hall J.; Husken D.; Haner R., Sequence-specific cleavage of RNA using macrocyclic lanthanide complexes conjugated to oligonucleotides: A structure activity study, *Nucleosides & Nucleotides*, 1997, 16: 1357-1368.
Hall J.; Husken D.; Haner R., Towards artificial ribonucleases: The sequence-specific cleavage of RNA in a duplex, *Nucl. Acid Res.*, 1996, 24: 3522-3526.
Häner R.; Hall J., The sequence-specific cleavage of RNA by artificial chemical ribonucleases. *Antisense and nucleic acid drug development*, 1997, 7: 423-430.
Häner R.; Hüsken D.; Hall J., Development of Artificial Ribonucleases Using Macrocyclic Lanthanide Complexes, *Chimia* 2000, 54:569-573.
Karelson, M.; Lomaka, A. Quantum-Chemical Modelling of the Tautomeric Equilibria of Modified Anionic Nucleic Acid Bases, *ARKIVOC*, 2001, 3, 51-62.
Komiyama, M., Sequence-specific and hydrolytic scission of DNA and RNA by lanthanide complex-oligoDNA hybrids, *J. Biochem.*, 1995, 118:665-670.
Komiyama, M. Sumaoka, J., Progress towards synthetic enzymes for phosphoester hydrolysis, *Current Opinion in Chemical Biology*, 1998, 2:751-757.
Kuzuya, A. et al., Conjugation of Various Acridines to DNA for Site-Selective RNA Scission by Lanthanide Ion, *Bioconjugate Chem.* 2002, 13: 365-366.
Kuzuya A.; Mizoguchi R.; Sasayama T.; Zhou J. M.; Komiyama M., Selective activation of two sites in RNA by acridine-bearing oligonucleotides for clipping of designated RNA fragments, *J. Am. Chem. Soc.*, 2004, 126: 1430-1436.
Magda, D., Metal Complex Conjugates of Antisense DNA Which Display Ribozyme-Like Activity, *J. Am. Chem. Soc.* 1997, 119:6947-6948.
Morrow, J. R., Artificial Ribonucleases, *Adv. Inorg. Biochem.*, 1994, 9:41-74.
Mesmaekar, A. D.; Haner, R.; Martin, P.; Moser, E. H. Antisense oligonucleotides, *Acc. Chem. Res.* 1995, 28: 366-374.
Shigekawa, et al., Extended x-ray absorption fine structure study on the cerium(IV)-induced DNA hydrolysis: Implication to the roles of 4 f orbitals in the catalysis *Appl. Phys. Lett.* 1999, 74: 460-462.
Stein, C. A.; The experimental use of antisense oligonucleotides: a guide for the perplexed. *J. Clin. Invest.* 2001, 108, 641-644.
Suen, W.; Spiro, T. G.; Sowers, L.; and Fresco, J. R. Identification by UV resonance Raman spectroscopy of an imino tautomer of 5-hydroxy-2'-deoxycytidine, a powerful base analog transition mutagen with a much higher unfavored tautomer frequency than that of the natural residue 2'-deoxycytidine. *Proc. Natl. Acad. Sci. USA* 1999, 96: 4500-4505.
Trawick, B N; Daniher, A T; Bashkin, J K, Inorganic Mimics of Ribonucleases and Ribozymes: From Random Cleavage to Sequence-Specific Chemistry to Catalytic Antisense Drugs, *Chem. Rev.* 1998, 98: 939-960.
Uhlmann, E.; Peyman, A: Antisense oligonucleotides: A new therapeutic principle. *Chemical Reviews* 1990, 90: 543-584.
Wallace S. S., Biological consequences of free radical-damaged DNA bases, *Free Radical Biology and Medicine*, 2002, 33:1-14.
Williams, N. H. et al., Structure and Nuclease Activity of Simple Dinuclear Metal Complexes Quantitative Dissection of the Role of Metal Ions, *Acc. Chem. Res.* 1999, 32: 485-493.

What is claimed is:

1. A compound comprising an oligonucleotide having from 5 to 150 nucleobases and a chelating moiety attached to the oligonucleotide, wherein at least 10% of said nucleobases are a modified nucleobase selected from the group consisting of: 5-mercaptocytosine, 5-mercaptouracil, 8-mercaptoguanine, 8-mercaptoadenine, 5-hydroxycytosine, 5-hydroxyuracil, 8-hydroxyadenine and 8-hydroxyguanine.

2. The compound of claim 1, wherein the modified nucleobase is a hydroxynucleobase selected from the group consisting of 5-hydroxycytosine, 5-hydroxyuracil, 8-hydroxyadenine and 8-hydroxyguanine.

3. The compound of claim 1 comprising from 10 to 100 nucleobases.

4. The compound of claim 1 comprising from 10 to 50 nucleobases.

5. The compound of claim 1 comprising from 20 to 30 nucleobases.

6. The compound according to claim 1, wherein at least 2 of the nucleobases are hydroxynucleobases selected from the group consisting of 5-hydroxycytosine, 5-hydroxyuracil, 8-hydroxyadenine and 8-hydroxyguanine.

7. The compound according to claim 6, wherein from 10% to 20% of the nucleobases are the hydroxynucleobases.

8. The compound according to claim 1, wherein the chelating moiety has a formula:

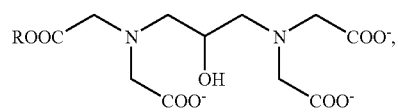

wherein R is the oligonucleotide.

9. The compound according to claim 1, wherein the chelating moiety has a formula:

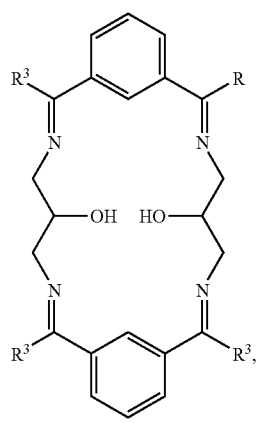

wherein R is the oligonucleotide; and
wherein $R^3$ are independently selected from the group consisting of hydrogen, $C_{1-8}$ alkane, $C_{2-8}$ alkene, $C_{2-8}$ alkyne, acylC$_{1-8}$alkane, cycloalkyl, heterocycloalkyl, aryl, heteroaryl, C$_{1-8}$alkylaryl, and C$_{1-8}$alkylheteroaryl.

10. The compound according to claim 1, wherein the chelating moiety has a formula:

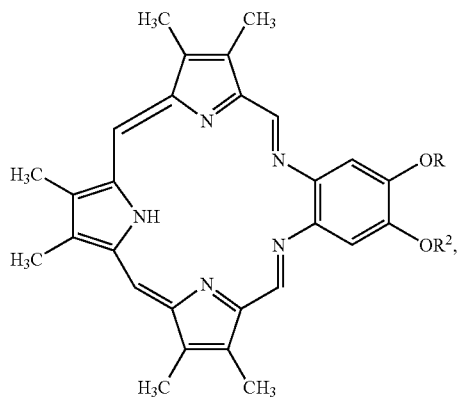

wherein R is the oligonucleotide; and
wherein R$^2$ is selected from C$_{1-8}$ alkyl, C$_{2-8}$ alkene, C$_{2-8}$ alkyne, aryl, heteroaryl, C$_{1-8}$alkylaryl, C$_{1-8}$alkylheteroaryl, and acylC$_{1-8}$alkane.

11. The compound according to claim 1, wherein the chelating moiety has a formula:

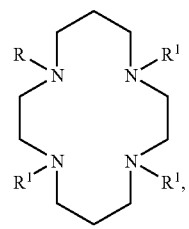

wherein R is the oligonucleotide; and
wherein R$^1$ are independently selected from the group consisting of hydrogen, C$_{1-8}$ alkane, C$_{2-8}$ alkene, C$_{2-8}$ alkyne, acylC$_{1-8}$alkane, cycloalkyl, heterocycloalkyl, aryl, heteroaryl, C$_{1-8}$alkylaryl, and C$_{1-8}$alkylheteroaryl.

12. The compound of claim 11, wherein R$^1$ are independently selected from hydrogen, —C(O)CF$_3$ and —CH$_2$Phenyl, and wherein Phenyl is substituted with H, OH, C(O)Oheterocycloalkyl, C(O)Oalkyl, or alkyl.

13. The compound according to claim 1, wherein the chelating moiety has a formula:

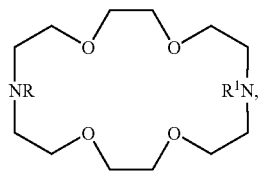

wherein R is the oligonucleotide; and
wherein R$^1$ is selected from the group consisting of hydrogen, C$_{1-8}$ alkane, C$_{2-8}$ alkene, C$_{2-8}$ alkyne, acylC$_{1-8}$alkane, cycloalkyl, heterocycloalkyl, aryl, heteroaryl, C$_{1-8}$alkylaryl, and C$_{1-8}$alkylheteroaryl.

14. The compound according to claim 1, wherein the chelating moiety has a formula:

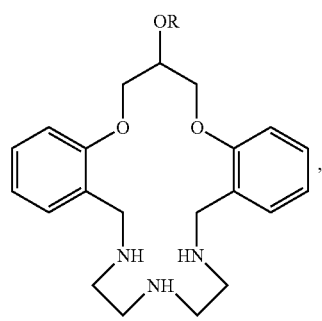

wherein R is the oligonucleotide.

15. The compound according to claim 1, wherein the chelating moiety has a formula:

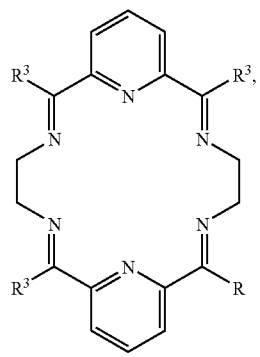

wherein R is the oligonucleotide; and
wherein R$^3$ are independently selected from the group consisting of hydrogen, C$_{1-8}$ alkane, C$_{2-8}$ alkene, C$_{2-8}$ alkyne, acylC$_{1-8}$alkane, cycloalkyl, heterocycloalkyl, aryl, heteroaryl, C$_{1-8}$alkylaryl, and C$_{1-8}$alkylheteroaryl.

16. The compound according to claim 1, wherein the chelating moiety has a formula:

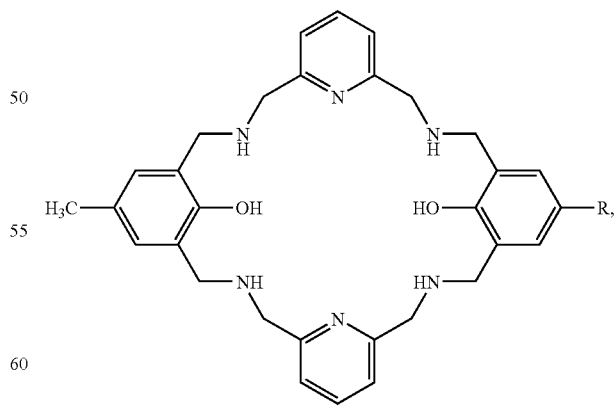

wherein R is the oligonucleotide.

17. The compound of claim 1, further comprising an ion of a metal, wherein the metal is selected from the group consisting of lanthanum, cerium, praseodymium, neodymium, promethium, samarium, europium, gadolinium, terbium, dysprosium, holmium, erbium, thulium, ytterbium, and lutetium.

18. The compound of claim 17, wherein the metal is europium or lanthanum.

19. A composition comprising the compound according to claim 1 and a pharmaceutically acceptable carrier.

20. The composition of claim 19 further comprising a delivery vehicle.

21. The composition of claim 20, wherein the delivery vehicle comprises a liposome, wherein the compound is contained within the liposome.

22. A method of inhibiting translation of a target nucleic acid comprising contacting the target nucleic acid with a compound according to claim 1, or a composition according to claim 19, under conditions that permit hybridizing of the compound to the target nucleic acid, wherein the hybridized compound inhibits translation of the target nucleic acid.

23. The method of claim 22 wherein the target nucleic acid is in an organism.

24. The method of claim 23 wherein the contacting comprises administering to the organism a composition that comprises the compound and a pharmaceutically acceptable carrier.

25. The method of claim 23, wherein the organism is a human or animal subject.

26. The method of claim 23, wherein the contacting comprises mixing the compound with a biological sample that comprises the target nucleic acid.

27. The method according to claim 22, wherein the hybridizing induces a cleavage of the target nucleic acid.

28. The method of claim 22, wherein the target nucleic acid is mRNA.

29. The method of claim 22, wherein the compound cleaves a bond of the target nucleic acid.

30. The method of claim 25, wherein the human or animal subject suffers from a viral infection, bacterial infection, microbial infection, fungal infection, or cancer.

31. A method of inhibiting translation of a nucleic acid in an organism, comprising:
  predicting or determining a nucleotide sequence of a target nucleic acid in an organism; and
  administering to the organism a composition according to claim 19, wherein the compound comprises a nucleotide sequence, wherein, under physiological conditions of the organism, said compound is sufficiently complementary to the nucleotide sequence of the target nucleic acid to hybridize thereto in the organism, thereby inhibiting translation of the nucleic acid.

32. The method according to claim 26, wherein the nucleotide sequence of the compound is fully complementary to all or a portion of the nucleotide sequence of the target nucleic acid.

33. A method of making a compound to inhibit translation of a nucleic acid of an organism under physiological conditions of the organism, comprising:
  a) determining a nucleotide sequence of a target nucleic acid;
  b) synthesizing a compound that comprises a chelating moiety attached to an oligonucleotide that comprises a nucleotide sequence that is sufficiently complementary to at least part of the nucleotide sequence of the target nucleic acid to permit the hybridization, wherein the oligonucleotide comprises from 5 to 150 nucleobases and wherein at least 10% of the nucleobases of the oligonucleotide are a modified nucleobase selected from the group consisting of: 5-mercaptocytosine, 5-mercaptouracil, 8-mercaptoguanine, 8-mercaptoadenine, 5-hydroxycytosine, 5-hydroxyuracil, 8-hydroxyadenine and 8-hydroxyguanine; and
  c) mixing said compound with an ion of a metal selected from the group consisting of lanthanum, cerium, praseodymium, neodymium, promethium, samarium, europium, gadolinium, terbium, dysprosium, holmium, erbium, thulium, ytterbium, and lutetium.

34. The method of claim 33, wherein the modified nucleobase is a hydroxynucleobase and is selected from the group consisting of 5-hydroxycytosine, 5-hydroxyuracil, 8-hydroxyadenine and 8-hydroxyguanine.

35. The method of claim 33 wherein the chelating moiety has a formula selected from the group consisting of:

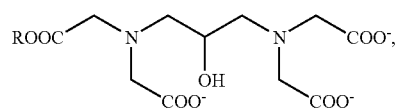

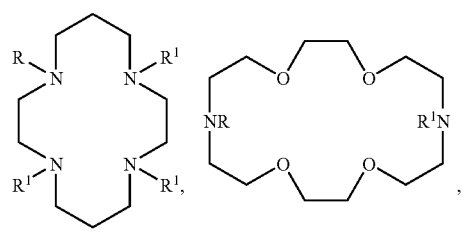

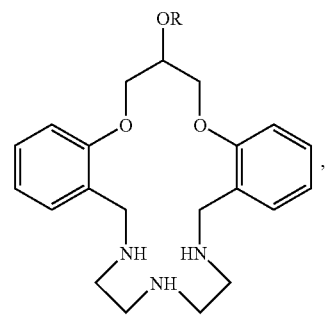

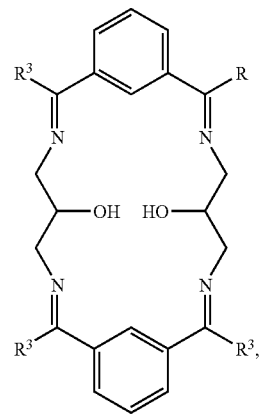

-continued

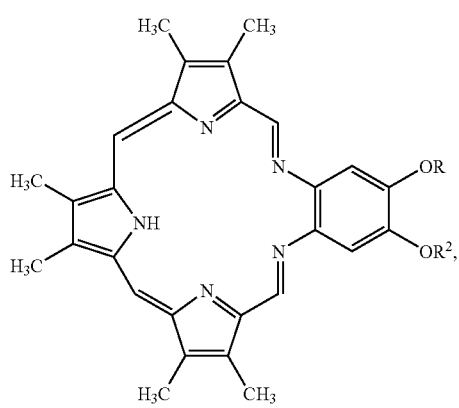

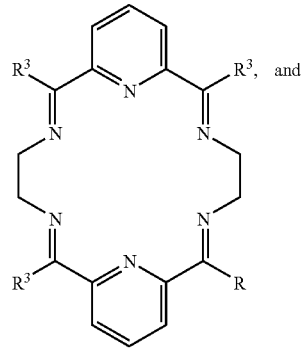

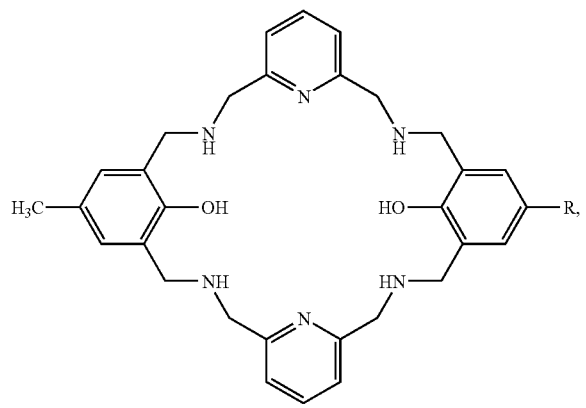

wherein R is the oligonucleotide,
R¹ and R³ are independently selected from the group consisting of hydrogen, $C_{1-8}$ alkane, $C_{2-8}$ alkene, $C_{2-8}$ alkyne, acyl$C_{1-8}$alkane, cycloalkyl, heterocycloalkyl, aryl, heteroaryl, $C_{1-8}$alkylaryl, and $C_{1-8}$alkylheteroaryl; and
wherein R² is independently selected from $C_{1-8}$ alkyl, $C_{2-8}$ alkene, $C_{2-8}$ alkyne, aryl, heteroaryl, $C_{1-8}$alkylaryl, $C_{1-8}$alkylheteroaryl, and acyl$C_{1-8}$alkane.

36. The method according to claim 33, wherein the conditions comprise human physiological conditions.

37. The compound according to claim 1, wherein the chelating moiety has a formula selected from the group consisting of:

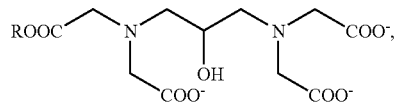

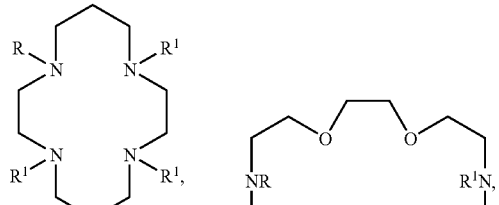

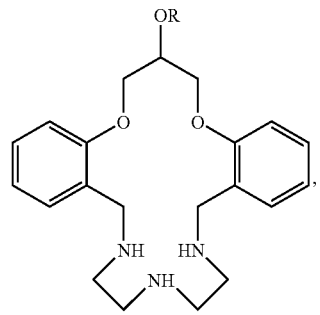

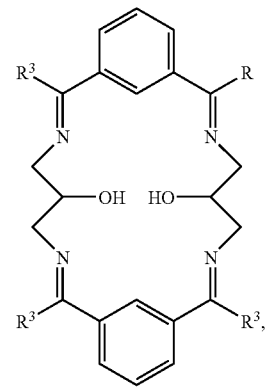

-continued

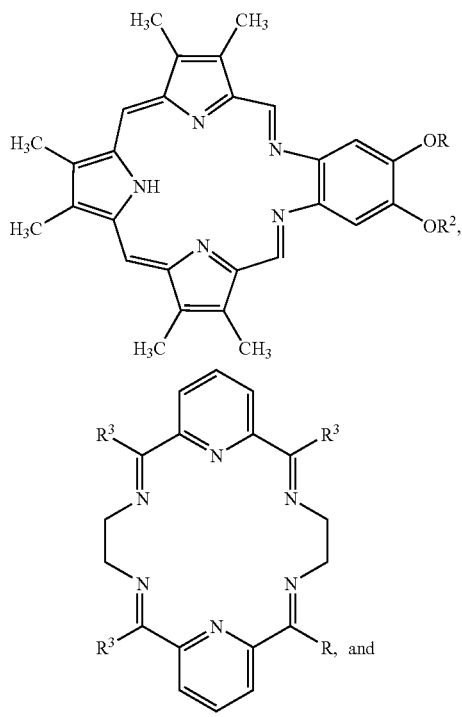

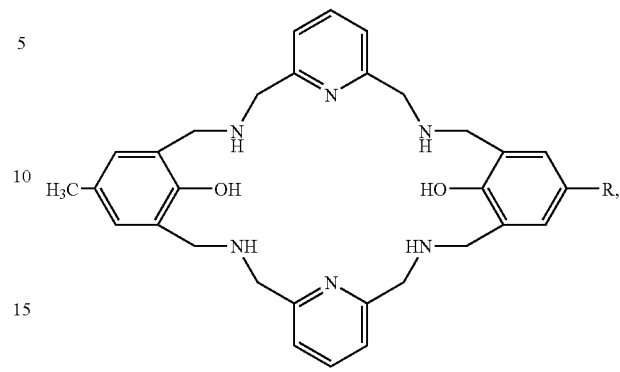

wherein R is the oligonucleotide, $R^1$ and $R^3$ are independently selected from the group consisting of hydrogen, $C_{1-8}$ alkane, $C_{2-8}$ alkene, $C_{2-8}$ alkyne, acyl$C_{1-8}$alkane, cycloalkyl, heterocycloalkyl, aryl, heteroaryl, $C_{1-8}$alkylaryl, and $C_{1-8}$alkylheteroaryl; and wherein $R^2$ is independently selected from $C_{1-8}$ alkyl, $C_{2-8}$ alkene, $C_{2-8}$ alkyne, aryl, heteroaryl, $C_{1-8}$alkylaryl, $C_{1-8}$alkylheteroaryl, and acyl$C_{1-8}$alkane.

* * * * *

SEQUENCE LISTING

<160> NUMBER OF SEQ ID NOS: 11

<210> SEQ ID NO 1
<211> LENGTH: 16
<212> TYPE: DNA
<213> ORGANISM: Artificial sequence
<220> FEATURE:
<223> OTHER INFORMATION: Synthetic primer
<220> FEATURE:
<221> NAME/KEY: misc_feature
<222> LOCATION: (16)..(16)
<223> OTHER INFORMATION: n=5-hydroxycytosine

<400> SEQUENCE: 1
gcagccaaaa cgtccn                                           16

<210> SEQ ID NO 2
<211> LENGTH: 15
<212> TYPE: DNA
<213> ORGANISM: Artificial sequence
<220> FEATURE:
<223> OTHER INFORMATION: Synthetic primer

<400> SEQUENCE: 2
gcagccaaaa cgtcc                                            15

<210> SEQ ID NO 3
<211> LENGTH: 6
<212> TYPE: DNA
<213> ORGANISM: Artificial sequence
<220> FEATURE:
<223> OTHER INFORMATION: Synthetic primer

<400> SEQUENCE: 3 ccttcg                                                       6

<210> SEQ ID NO 4
<211> LENGTH: 16
<212> TYPE: DNA
<213> ORGANISM: Artificial sequence
<220> FEATURE:
<223> OTHER INFORMATION: Synthetic primer
<220> FEATURE:
<221> NAME/KEY: misc_feature
<222> LOCATION: (16)..(16)
<223> OTHER INFORMATION: n=5-hydroxycytosine or 5-hydroxyuracil

<400> SEQUENCE: 4
gcagccaaaa cgtccn                                           16

<210> SEQ ID NO 5
<211> LENGTH: 7
<212> TYPE: DNA
<213> ORGANISM: Artificial sequence
<220> FEATURE:
<223> OTHER INFORMATION: Synthetic primer
<220> FEATURE:
<221> NAME/KEY: misc_feature
<222> LOCATION: (7)..(7)
<223> OTHER INFORMATION: n=5-hydroxycytosine or 5-hydroxyuracil

<400> SEQUENCE: 5 ccttcgn                                                      7

<210> SEQ ID NO 6
<211> LENGTH: 20

```
<212> TYPE: DNA
<213> ORGANISM: Artificial sequence
<220> FEATURE:
<223> OTHER INFORMATION: Synthetic primer
<220> FEATURE:
<221> NAME/KEY: misc_feature
<222> LOCATION: (20)..(20)
<223> OTHER INFORMATION: n=5-hydroxycytosine or cytosine

<400> SEQUENCE: 6
cttctggccg tttacgtcgn                                        20

<210> SEQ ID NO 7
<211> LENGTH: 20
<212> TYPE: DNA
<213> ORGANISM: Artificial sequence
<220> FEATURE:
<223> OTHER INFORMATION: Synthetic primer

<400> SEQUENCE: 7
gcgacgtaaa cggccagaag                                        20

<210> SEQ ID NO 8
<211> LENGTH: 20
<212> TYPE: DNA
<213> ORGANISM: Artificial sequence
<220> FEATURE:
<223> OTHER INFORMATION: Synthetic primer
<220> FEATURE:
<221> NAME/KEY: misc_feature
<222> LOCATION: (6)..(6)
<223> OTHER INFORMATION: n=7,8-dihydro-8-oxoguanine
<220> FEATURE:
<221> NAME/KEY: misc_feature
<222> LOCATION: (7)..(7)
<223> OTHER INFORMATION: n=7,8-dihydro-8-oxoguanine
<220> FEATURE:
<221> NAME/KEY: misc_feature
<222> LOCATION: (10)..(10)
<223> OTHER INFORMATION: n=7,8-dihydro-8-oxoguanine
<220> FEATURE:
<221> NAME/KEY: misc_feature
<222> LOCATION: (16)..(16)
<223> OTHER INFORMATION: n=7,8-dihydro-8-oxoguanine
<220> FEATURE:
<221> NAME/KEY: misc_feature
<222> LOCATION: (19)..(19)
<223> OTHER INFORMATION: n=7,8-dihydro-8-oxoguanine

<400> SEQUENCE: 8
cttctnnccn tttacntcnc                                        20

<210> SEQ ID NO 9
<211> LENGTH: 20
<212> TYPE: DNA
<213> ORGANISM: Artificial sequence
<220> FEATURE:
<223> OTHER INFORMATION: Synthetic primer
<220> FEATURE:
<221> NAME/KEY: misc_feature
<222> LOCATION: (6)..(6)
<223> OTHER INFORMATION: n=7,8-dihydro-8-oxoguanine

<400> SEQUENCE: 9
cttctngccg tttacgtcgc                                        20

<210> SEQ ID NO 10
<211> LENGTH: 20
<212> TYPE: DNA
<213> ORGANISM: Artificial sequence
<220> FEATURE:
```

```
-continued

<223> OTHER INFORMATION: Synthetic primer
<220> FEATURE:
<221> NAME/KEY: misc_feature
<222> LOCATION: (6)..(6)
<223> OTHER INFORMATION: n=7,8-dihydro-8-oxoguaunine
<220> FEATURE:
<221> NAME/KEY: misc_feature
<222> LOCATION: (10)..(10)
<223> OTHER INFORMATION: n=7,8-dihydro-8-oxoguaunine

<400> SEQUENCE: 10
cttctngccn tttacgtcgc                                              20

<210> SEQ ID NO 11
<211> LENGTH: 20
<212> TYPE: DNA
<213> ORGANISM: Artificial sequence
<220> FEATURE:
<223> OTHER INFORMATION: Synthetic primer
<220> FEATURE:
<221> NAME/KEY: misc_feature
<222> LOCATION: (6)..(6)
<223> OTHER INFORMATION: n=7,8-dihydro-8-oxoguanine
<220> FEATURE:
<221> NAME/KEY: misc_feature
<222> LOCATION: (10)..(10)
<223> OTHER INFORMATION: n=7,8-dihydro-8-oxoguanine
<220> FEATURE:
<221> NAME/KEY: misc_feature
<222> LOCATION: (19)..(19)
<223> OTHER INFORMATION: n=7,8-dihydro-8-oxoguanine

<400> SEQUENCE: 11
cttctngccn tttacgtcnc                                              20
```